United States Patent [19]
Nanbu et al.

[11] Patent Number: 6,128,084
[45] Date of Patent: Oct. 3, 2000

[54] EVALUATION METHOD OF SEMICONDUCTOR LAYER, METHOD FOR FABRICATING SEMICONDUCTOR DEVICE, AND STORAGE MEDIUM

[75] Inventors: Yuko Nanbu, Otsu; Satoshi Shibata, Takaoka, both of Japan

[73] Assignee: Matsushita Electronics Corporation, Osaka, Japan

[21] Appl. No.: 09/214,826

[22] PCT Filed: Jun. 10, 1998

[86] PCT No.: PCT/JP98/02567

§ 371 Date: Jan. 13, 1999

§ 102(e) Date: Jan. 13, 1999

[87] PCT Pub. No.: WO98/57146

PCT Pub. Date: Dec. 17, 1998

[30] Foreign Application Priority Data

Jun. 11, 1997 [JP] Japan ................................. 9-153980

[51] Int. Cl.⁷ ................................. G01J 4/00; G02F 1/01
[52] U.S. Cl. ........................... 356/369; 356/381; 250/225
[58] Field of Search ................................. 356/364, 367, 356/368, 369, 381, 382; 250/225

[56] References Cited

U.S. PATENT DOCUMENTS

| | | | |
|---|---|---|---|
| 5,229,304 | 7/1993 | Chang et al. | 437/174 |
| 5,978,074 | 11/1999 | Opsal et al. | 356/369 |

FOREIGN PATENT DOCUMENTS

| | | |
|---|---|---|
| 59-50927 | 12/1984 | Japan . |
| 4-501175 | 2/1992 | Japan . |
| 5-249031 | 9/1993 | Japan . |
| 6-50880 | 2/1994 | Japan . |

*Primary Examiner*—Frank G. Font
*Assistant Examiner*—Zandra V. Smith
*Attorney, Agent, or Firm*—McDermott, Will & Emery

[57] ABSTRACT

Measurement light, which has been emitted from a Xe light source (20) and then linearly polarized by a polarizer (21), is made to be incident at a tilt angle on a region in a silicon substrate (11) with crystallinity disordered by the implantation of dopant ions. And the spectra of $\cos\Delta$ and $\tan\psi$ are measured with a variation of the measurement light, where $\Delta$ is a phase difference between respective components in p and s directions as to the light reflected as an elliptically-polarized ray, and $\psi$ is a ratio between the amplitudes of these components. By correlating in advance the spectral patterns of $\cos\Delta$ and so on with the thickness of an amorphous region through a destructive test or the like, or by paying special attention to characteristic parts of the patterns of $\cos\Delta$ and so on, the thickness or the degree of disordered crystallinity of the amorphous region is estimated. Also, since a variation in the thickness of the amorphous region can be identified based on a variation of $\cos\Delta$ before and after a heat treatment, a temperature of the heat treatment can be sensed based on the variation of the thickness. Thus, an evaluation method allowing for nondestructive estimation of the thickness and the degree of disorder of a region, having crystallinity disordered by implanting dopant ions into a semiconductor region at a high level, can be provided.

33 Claims, 31 Drawing Sheets

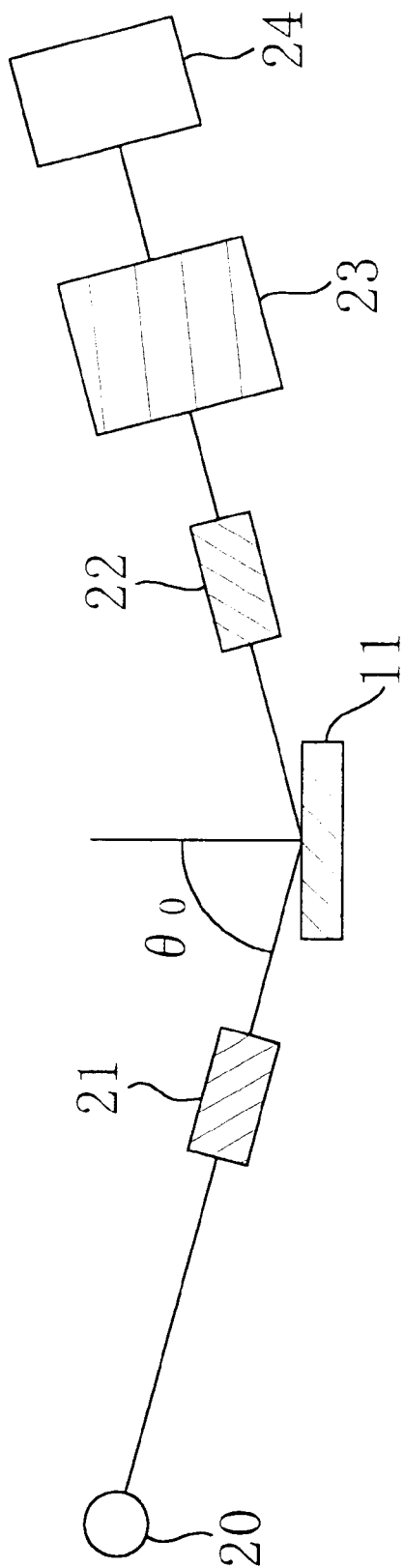

Doped

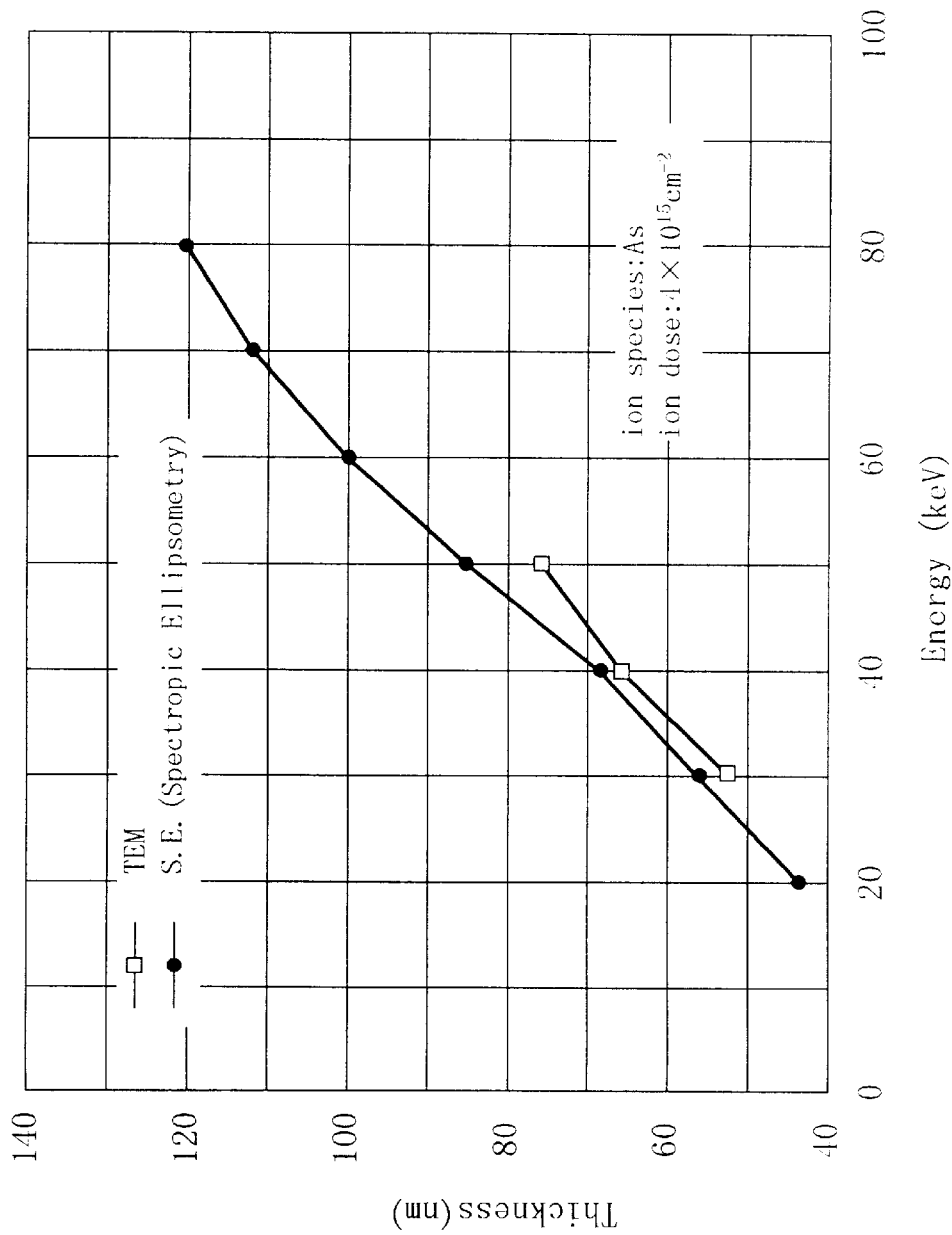

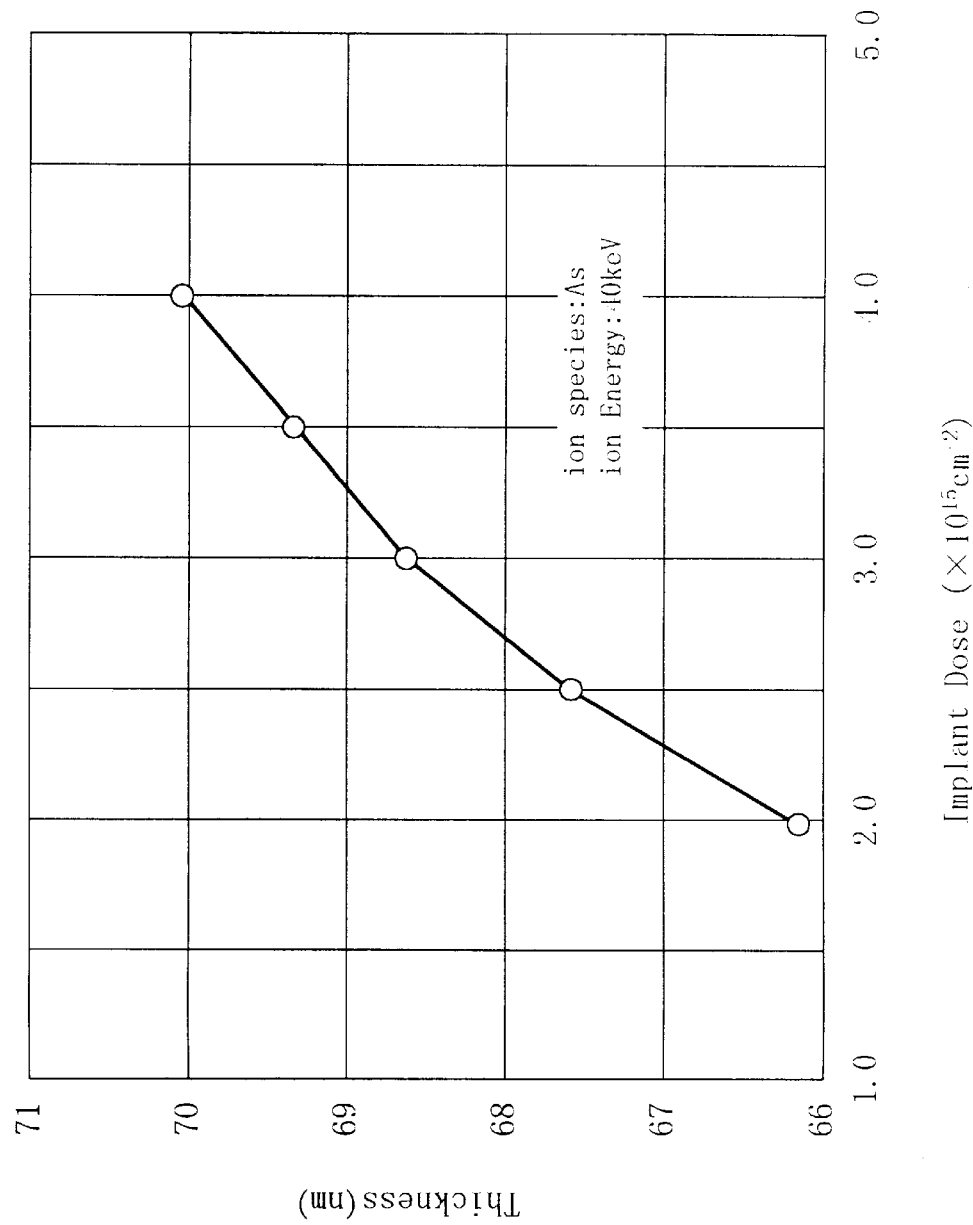

Sheet resistance method
Resistance:85.5Ω
In-plane uniformity:1.16%

Thermal wave method
TW value:23332TW
In-plane uniformity:0.13%

Spectroscopic ellipsometry
Thickness:69nm
In-plane uniformity:0.153%

Undoped

Implanter: Company A
Ion species: As$^+$
Implant energy: 60KeV
Implant Dose : $1 \times 10^{14} cm^{-2}$ Implanter: Company A
Ion species: As$^+$
Implant energy: 60KeV
Implant Dose : 5×10$^{13}$cm$^{-2}$ Implanter:Company B
Ion species:As$^+$
Implant energy:60KeV
Implant Dose :5×10$^{13}$cm$^{-2}$ Implanter: Company B
Ion species: $As^+$
Implant energy: 60KeV
Implant Dose : $1 \times 10^{14} cm^{-2}$
Current density: $615 \mu A/cm^2$ Implanter:Company B
Ion species:As⁻
Implant energy:60KeV
Implant Dose : $1 \times 10^{14} cm^{-2}$
Current density:2000 $\mu A/cm^2$

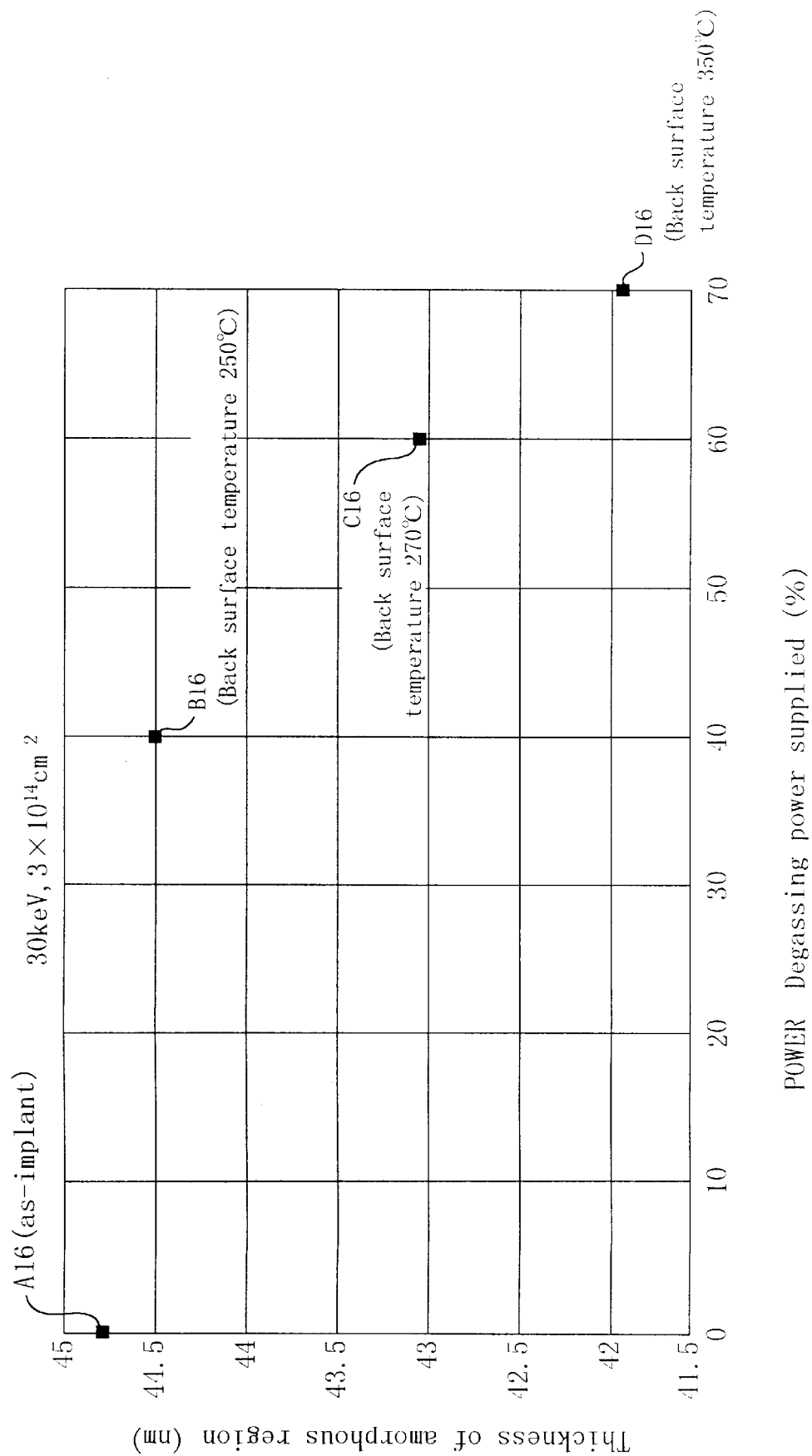

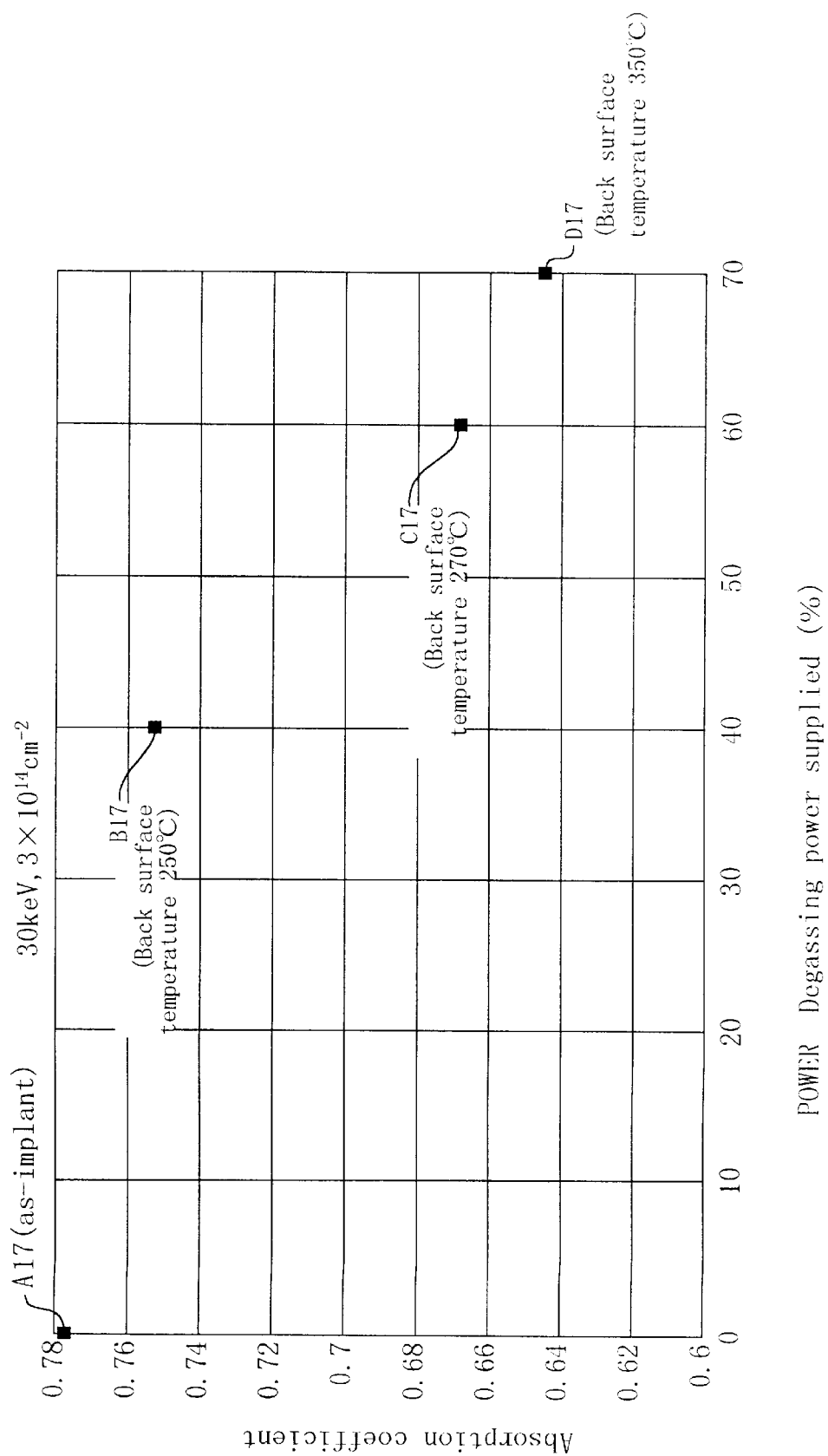

Data about △

| Time | 0 sec. | 10 sec. | 60 sec. |
|---|---|---|---|
| Thickness of amorphous region | 44.8nm | 32nm | 15nm |
| Recovery rate | 77nm/min. | | 20.4nm/min. |

Annealing at 550°C

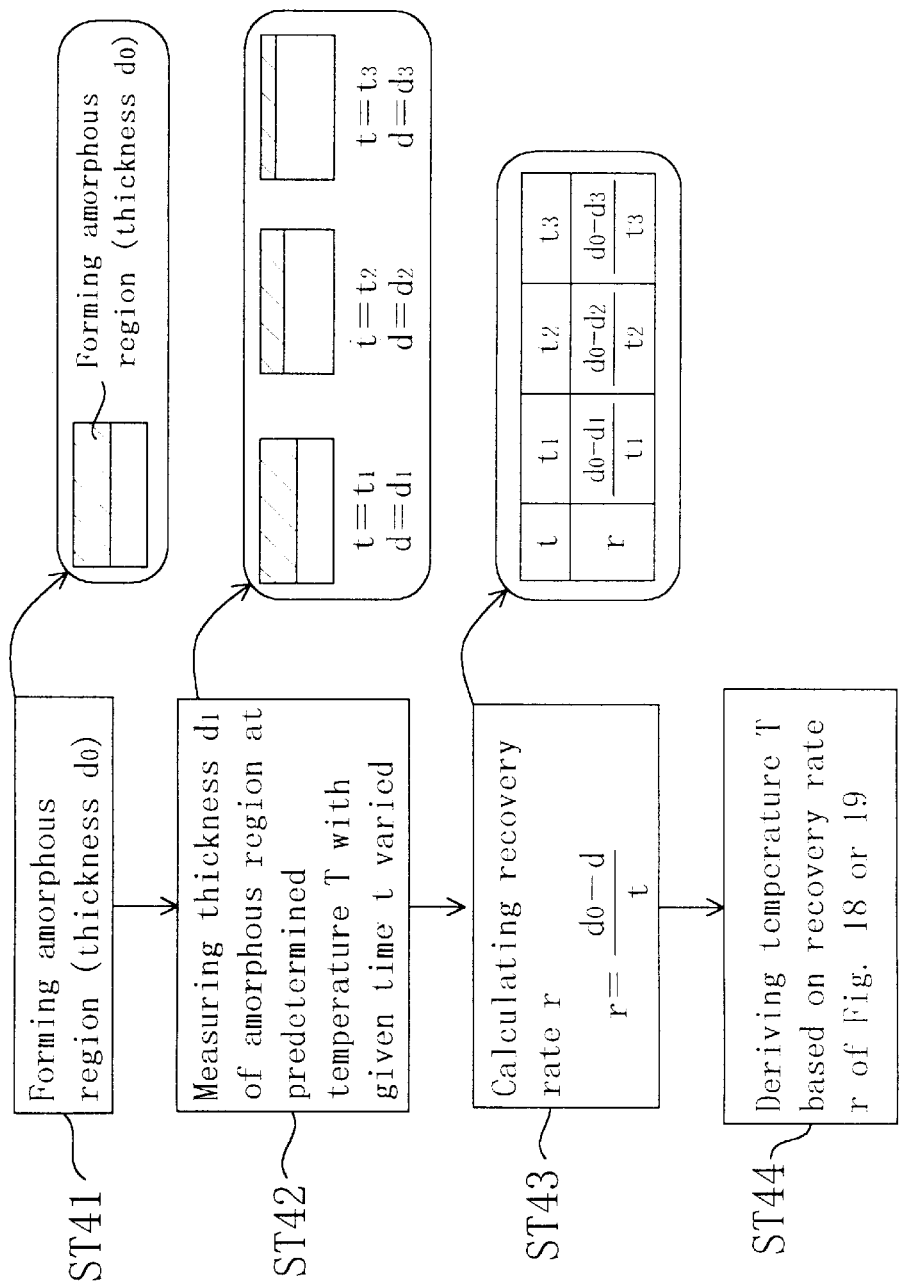

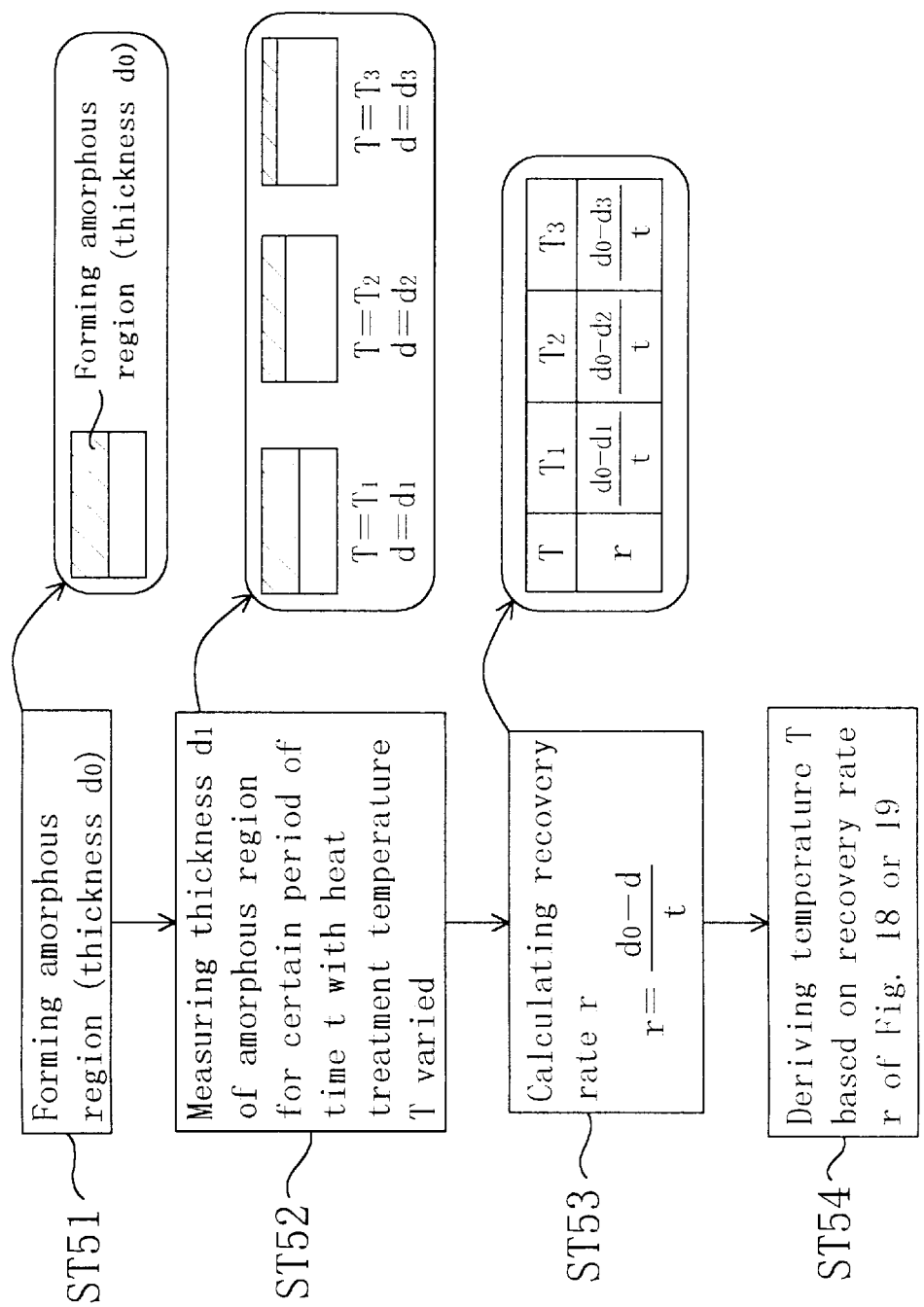

First correlation

|   | $E_1$ | $E_1$ | $E_1$ | ......... |
|---|---|---|---|---|
| $D_1$ | $d_{11}$ | $d_{12}$ | $d_{13}$ | ......... |
| $D_2$ | $d_{21}$ | $d_{22}$ | $d_{23}$ | ......... |
| $D_3$ | $d_{31}$ | $d_{32}$ | $d_{33}$ | ......... |
| ⋮ | ⋮ | ⋮ | ⋮ | ⋱ |

Second correlation

|   | $E_1$ | $E_2$ | $E_3$ | ......... |
|---|---|---|---|---|
| $D_1$ | $S_{11}$ | $S_{12}$ | $S_{13}$ | ......... |
| $D_2$ | $S_{21}$ | $S_{22}$ | $S_{23}$ | ......... |
| $D_3$ | $S_{31}$ | $S_{32}$ | $S_{33}$ | ......... |
| ⋮ | ⋮ | ⋮ | ⋮ | ⋱ |

Fig. 33

| | First embodiment | Second embodiment | Third embodiment |
|---|---|---|---|
| First specific example | Thickness of amorphous region | Actual temperature on wafer surface | Control over ion implantation step |
| Second specific example | In-plane distribution of amorphous region | Film quality of amorphous region | Control over CVD and sputtering steps |
| Third specific example | Determination on how easy amorphous region is formed | Variation in recovery rate with time | |
| Fourth specific example | — | Recovery at 450°C or less | |
| Fifth specific example | — | Temperature distribution on wafer plane | |
| Sixth specific example | — | Film quality distribution on wafer plane | |

EVALUATION METHOD OF SEMICONDUCTOR LAYER, METHOD FOR FABRICATING SEMICONDUCTOR DEVICE, AND STORAGE MEDIUM

TECHNICAL FIELD

The present invention relates to a method for optically evaluating the characteristic of an amorphous region with crystallinity disordered by dopant ions implanted at a high level, a method for measuring a temperature and a method for fabricating a semiconductor device utilizing such evaluation, and a storage medium used for automatically making the evaluation.

BACKGROUND ART

In a fabrication process of a semiconductor device such as a transistor, when source/drain regions for a MOSFET, an emitter diffusion layer for a bipolar transistor and so on are formed, for example, ion implantation for accelerating and implanting ions such as P, As and B into a semiconductor substrate, a polysilicon layer or an amorphous silicon film has heretofore been utilized as a means for accurately controlling doping level of the dopant, depth of a region to be doped and the like. Recently, in order to meet a demand for miniaturization of semiconductor devices, the dopant concentration and thickness of a region formed by the ion implantation need to be controlled even more precisely.

For example, it is known that, when silicon atoms are scattered out of the normal sites thereof by dopant ions implanted into a single crystalline layer, an amorphous region is formed by these recoil silicon atoms. As a means for measuring the thickness and the like of such an amorphous region formed by these recoil silicon ions, Rutherford backscattering spectrometry (RBS) and the photograph of a cross section taken with a transmission electron microscope (TEM) are conventionally adopted.

Ion implant energy and dose of dopant ions implanted into a silicon substrate are conventionally estimated by 4-terminal sheet resistance measurement or thermal wave method. Similarly, the uniformity of the dopant concentration of an ion implanted layer formed on a silicon substrate in a silicon wafer by the ion implantation is also estimated by 4-terminal sheet resistance measurement or thermal wave method.

On the other hand, ellipsometry, obtaining information such as complex refractive index and thickness by making linearly-polarized light incident on the surface of a substrate at a tilt angle and measuring an elliptical shape of elliptically-polarized light reflected from the substrate surface, is known as a simple optical evaluation method.

Problems to be Solved

However, when these evaluation methods are applied to the characterization during the actual fabrication process of a semiconductor device, the following problems arise. And it has been difficult to evaluate whether or not the implantation conditions are appropriate for a region implanted with ions at a high level, in particular.

First, the RBS and the TEM are destructive test methods, and hence are not suitable for evaluation in the production line of semiconductor devices.

Furthermore, when a region implanted with a dopant at a high level is evaluated by the sheet resistance measurement, the measurement is considerably affected by a heat treatment because accelerated diffusion is locally caused due to the damage resulting from the ion implantation. Accordingly, it is impossible to evaluate the ion implantation conditions by themselves.

In accordance with the thermal wave method, the ion implant energy and the concentration of implanted ions are estimated by measuring a damage in an implanted layer. In a region implanted with an impurity at a high level, however, it is difficult to identify the difference in implant doses, because the degree of the damage reaches a saturation region of detection sensitivity. In addition, since a value detected is not an absolute magnitude but a relative value, high detection sensitivity cannot be expected as to such a region implanted at a high level.

The present invention was made in view of these problems. The object of the present invention is to provide an evaluation method of a semiconductor layer, by which the thickness of an amorphous region, having crystallinity disordered by dopant ions implanted into the semiconductor layer at a high level, and the distribution of the thicknesses in the surface of a substrate can be nondestructively estimated with satisfactory reproducibility. Another object of the present invention is to provide a method for fabricating a semiconductor device utilizing this evaluation method of a semiconductor layer. Still another object of the present invention is to provide a storage medium for making a computer execute the evaluation of a semiconductor layer.

DISCLOSURE OF INVENTION

In order to accomplish this object, according to the present invention, a parameter regarding a complex refractive index and the spectral pattern thereof obtained by a spectroscopic ellipsometry are utilized for estimating a physical quantity of an amorphous region.

An evaluation method of a semiconductor layer according to the present invention includes the steps of: i) making linearly-polarized measurement light incident on the surface of the semiconductor layer at a tilt angle defined with respect to a normal crossing the surface at right angles, the semiconductor layer including an amorphous region with crystallinity disordered by dopant ions implanted into a substrate, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis; ii) deriving at least $\cos\Delta$ as to the reflected ray of the measurement light reflected as an elliptically-polarized ray from the semiconductor layer, where $\Delta$ is a phase difference between p and s components; iii) measuring the spectrum of at least the $\cos\Delta$ in accordance with a variation in the wavelength of the measurement light; and iv) estimating a physical quantity of the amorphous region based on at least the spectrum of the $\cos\Delta$.

In accordance with this method, if the wavelength of the measurement light, detected as an elliptically-polarized ray, is varied, then $\cos\Delta$, one of the parameters regarding the complex refractive index of the semiconductor layer, and other parameters are obtained. In addition, the spectra of $\cos\Delta$ and so on are obtained as information on the thickness and film quality of the amorphous region. As a result, the physical quantity of the semiconductor layer, subjected to the ion implantation, can be estimated nondestructively.

In the evaluation method of a semiconductor layer, the transparency, presence or absence and thickness of the amorphous region can be estimated in the step iv).

When the thickness of the semiconductor layer is estimated, the method further includes the step of preparing a correlation between the thickness of the amorphous region and at least the spectrum of cosΔ. In the step iv), the thickness of the amorphous region in the semiconductor layer can be determined by reference to the correlation about at least the spectrum of cosΔ obtained in the step ii).

In the step of preparing the correlation, a relationship between implant energy and the thickness of the amorphous region and a relationship between the spectrum of cosΔ and implant energy are prepared as first and second correlations, respectively, with regard to each particular ion implant dose. And in the step iv), after the implant energy of the ions implanted into the semiconductor layer has been obtained by reference to the second correlation about the spectrum of cosΔ obtained in the step ii), the thickness of the amorphous region in the semiconductor layer can be determined by reference to the first correlation about the implant energy obtained.

Alternatively, in the step of preparing the correlation, a relationship between an ion implant dose and the thickness of the amorphous region and a relationship between the spectrum of cosΔ and an ion implant dose are prepared as first and second correlations, respectively, with regard to each particular implant energy. And in the step iv), after the implant dose of the ions implanted into the semiconductor layer has been obtained by reference to the second correlation about the spectrum of cosΔ obtained in the step ii), the thickness of the amorphous region in the semiconductor layer can be determined by reference to the first correlation about the ion implant dose obtained.

In accordance with these methods, if the first and second correlations are prepared, the thickness of the amorphous region can be estimated nondestructively and with high reproducibility by reference to these correlations about the spectrum of cosΔ obtained through the measurement by the spectroscopic ellipsometry.

Furthermore, in the step of preparing the correlation, a relationship between implant energy and the thickness of the amorphous region is prepared as a first correlation with regard to each particular ion implant dose, and a relationship between a wavelength corresponding to a local maximum of cos Δ within a predetermined wavelength region of the spectrum of cosΔ and implant energy is prepared as a second correlation. The wavelength region is defined by making the ion implant dose constant and the implant energy variable. And in the step iv), after the implant energy of the ions implanted into the semiconductor layer has been obtained by reference to the second correlation about the spectrum of cosΔ obtained in the step ii), the thickness of the amorphous region in the semiconductor layer can be determined by reference to the first correlation about the implant energy obtained.

Alternatively, in the step of preparing the correlation, a relationship between an implant dose and the thickness of the amorphous region is prepared as a first correlation with regard to each particular implant energy, and a relationship between a wavelength corresponding to a local maximum of cos Δ within a predetermined wavelength region of the spectrum of cosΔ and an implant dose is prepared as a second correlation. The wavelength region is defined by making the implant energy constant and the implant dose variable. And in the step iv), after the implant dose of the ions implanted into the semiconductor layer has been obtained by reference to the second correlation about the spectrum of cosΔ obtained in the step ii), the thickness of the amorphous region in the semiconductor layer can be determined by reference to the first correlation about the ion implant dose obtained.

In accordance with these methods, if the first and second correlations are prepared, the thickness of the amorphous region can be estimated nondestructively and with high reproducibility by reference to these correlations about the spectrum of cosΔ obtained through the measurement by the spectroscopic ellipsometry.

According to these two methods, the thickness of the amorphous region can be detected easily and rapidly.

By performing the steps i) to iv) on a plurality of amorphous regions in the semiconductor layer, the distribution of thicknesses of the amorphous regions in the semiconductor layer can be estimated.

Furthermore, in accordance with this evaluation method of a semiconductor layer, the following specific information on the physical quantity of the amorphous region can be obtained. In the step iv), the degree of recovery of the amorphous region responsive to ion beams can be estimated. Alternatively, in the step iv), the performance of implanters can be evaluated based on at least the spectra of cosΔ of two amorphous regions formed using two different implanters on the same implant conditions.

The evaluation method of a semiconductor layer may further include the steps of: deriving tanψ as to the reflected ray of the measurement light, where ψ is a ratio of the amplitude of a p component to that of an s component; and measuring the spectrum of the tanψ with the wavelength of the measurement light varied. In the step of estimating the physical quantity of the amorphous region, the physical quantity of the amorphous region can be estimated with the shape of the spectrum of the tan ψ taken into consideration.

In accordance with this method, more accurate information on the amorphous region can be obtained based on cosΔ and tan ψ, which are two parameters regarding the complex refractive index.

In the evaluation method of a semiconductor layer, a first thickness of the amorphous region may be determined by performing the steps i) through iv) on the semiconductor layer before a heat holding process is conducted. The method may further include the steps of: determining a second thickness of the amorphous region by performing the steps i) through iv) on the semiconductor layer after the heat holding process has been conducted on the semiconductor layer; and measuring a temperature of the heat holding process based on a recovery rate derived from the first and second thicknesses of the amorphous region and a time of the heat holding process.

In accordance with this method, the temperature at the upper surface of a substrate can also be sensed unlike a method using a wafer provided with a temperature sensor. In addition, the temperature can be measured in a substantially unlimited range.

The evaluation method of a semiconductor layer may further include the step of finding a correlation between a temperature of the heat holding process conducted at a temperature equal to or lower than 450° C. and a decrease in thickness of an amorphous region. In the step iv), the temperature of the heat holding process can be measured based on the correlation.

In accordance with this method, the evaluation can be done rapidly.

In the evaluation method of a semiconductor layer, the temperature of the heat holding process may be measured as to each of a plurality of amorphous regions in the substrate. And the distribution of temperatures in the substrate or in a processing system can be measured based on the temperatures held at the amorphous regions.

In accordance with this method, more detailed information can be obtained, and therefore, the results of evaluation are applicable to fine adjustment in conditions for various types of heat treatments, for example.

A first method for fabricating a semiconductor device is a method for fabricating a semiconductor device on a semiconductor layer in a substrate. The method includes the steps of: i) forming an amorphous region with crystallinity disordered by implanting dopant ions into the semiconductor layer; ii) making linearly-polarized measurement light incident on the surface of the semiconductor layer, where the amorphous region has been formed, at a tilt angle defined with respect to a normal crossing the surface at right angles, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis, and measuring at least the spectrum of cos$\Delta$ in accordance with a variation in the wavelength of the measurement light as to the reflected ray of the measurement light reflected as an elliptically-polarized ray from the semiconductor layer, where $\Delta$ is a phase difference between p and s components; and iii) estimating a physical quantity of the amorphous region based on at least the spectrum of the cos$\Delta$ obtained in the step ii).

The first method for fabricating a semiconductor device may further include the step of preparing a correlation between the thickness of the amorphous region and at least the spectrum of cos$\Delta$. In the step iii), the thickness of the amorphous region in the semiconductor layer can be determined by reference to the correlation about at least the spectrum of cos$\Delta$ obtained in the step ii).

In accordance with this method, if the wavelength of the measurement light, detected as an elliptically-polarized ray, is varied, then cos$\Delta$, one of the parameters regarding the complex refractive index of the amorphous region, and other parameters can be obtained. In addition, the shapes of the spectra of cos$\Delta$ and so on are obtained as information on the physical quantity of the amorphous region, i.e., the degree of disorder, the thickness of the amorphous region and the like. Accordingly, by nondestructively estimating the physical quantity of the amorphous region with crystallinity disordered owing to the ion implantation, it can be determined whether or not ion implantation conditions are appropriate. And if the ion implantation conditions are inappropriate, then these conditions can be modified.

The first method for fabricating a semiconductor device may further include the step of changing ion implantation conditions for the step ii) based on the result of evaluation of the physical quantity of the amorphous region obtained in the step iii).

In accordance with this method, the fabrication process can be improved by feeding back the measurement results obtained by the spectroscopic ellipsometry to the ion implantation process step.

The first method for fabricating a semiconductor device may further include the step of determining whether or not the substrate including the amorphous region is acceptable based on the result of evaluation of the physical quantity of the amorphous region obtained in the step iii).

In accordance with this method, it is possible to determine whether the final product will be good or bad during the fabrication process of semiconductor devices. Accordingly, the throughput can be improved by canceling subsequent process steps on defective products or by additional implantation.

A second method for fabricating a semiconductor device according to the present invention is a method for fabricating a semiconductor device on a semiconductor layer in a substrate. The method includes the steps of: i) forming an amorphous region with crystallinity disordered by implanting dopant ions into the semiconductor layer; ii) conducting a process of holding the temperature of the amorphous region at a predetermined temperature; iii) making linearly-polarized measurement light incident on the surface of the semiconductor layer at a tilt angle defined with respect to a normal crossing the surface at right angles, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis, and measuring at least the spectrum of cos$\Delta$ in accordance with a variation in the wavelength of the measurement light as to the reflected ray of the measurement light reflected as an elliptically-polarized ray from the semiconductor layer, where $\Delta$ is a phase difference between p and s components; and iv) estimating a physical quantity of the amorphous region based on at least the spectrum of cos$\Delta$ obtained in the step iii).

In accordance with this method, if the wavelength of the measurement light, detected as an elliptically-polarized ray, is varied, then cos$\Delta$, one of the parameters regarding the complex refractive index of the amorphous region, and other parameters can be obtained. In addition, the shapes of the spectra of cos$\Delta$ and so on are obtained as information on the physical quantity of the amorphous region, i.e., the degree of disorder, the thickness of the amorphous region and the like. Accordingly, by nondestructively estimating the physical quantity of the semiconductor layer with crystallinity disordered owing to the ion implantation, it can be determined whether or not conditions for a subsequent heat treatment are appropriate. And if the heat treatment conditions are inappropriate, then these conditions can be modified.

The second method for fabricating a semiconductor device may further include the step of preparing a correlation between the thickness of the amorphous region and at least the spectrum of cos$\Delta$. In the step iv), the thickness of the amorphous region in the semiconductor layer can be determined by reference to the correlation about at least the spectrum of cos$\Delta$ obtained in the step ii).

In accordance with this method, since the thickness of the amorphous region can be found, it is possible to determine how far activation has reached during a process such as annealing. In addition, the level of appropriate conditions for annealing a substrate can also be determined.

The second method for fabricating a semiconductor device may further include the steps of: estimating the thickness of the amorphous region prior to the step ii) by performing the same process steps as the steps iii) and iv) posterior to the step i) and prior to the step ii); and obtaining a variation in the thickness of the amorphous region before and after the step ii) is performed.

In the second method for fabricating a semiconductor device, in the step iv), a reflection factor of the measurement light reflected from the amorphous region may be calculated based on a ratio between the intensity of the incident and that reflected rays of the measurement light. And film quality of the amorphous region can be evaluated based on the reflection factor.

A third method for fabricating a semiconductor device according to the present invention is a method for fabricating a semiconductor device on a semiconductor layer in a substrate. The method includes the steps of: i) forming an amorphous region with crystallinity disordered by implanting dopant ions into the semiconductor layer; ii) conducting a process of holding the temperature of the amorphous region at a predetermined temperature; iii) making linearly-polarized measurement light incident on the surface of the semiconductor layer at a tilt angle defined with respect to a normal crossing the surface at right angles, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis, and measuring at least the spectra of cosΔ before and after the process in the step ii) is performed as to the reflected ray of the measurement light reflected as an elliptically-polarized ray from the semiconductor layer, where Δ is a phase difference between p and s components; iv) measuring a variation in the thickness of the amorphous region before and after the process in the step ii) is performed based on at least the variation in the spectrum of cosΔ; and v) measuring a temperature of the heat holding process based on a recovery rate calculated based on the variation in the thickness of the amorphous region before and after the process is performed and a time of the heat holding process.

The third method for fabricating a semiconductor device may further include the step of preparing a correlation between a temperature of the heat holding process conducted at a temperature equal to or lower than 450° C. and a decrease in thickness of the amorphous region. In the step iv), the temperature of the heat holding process can be measured based on the correlation.

The present invention also provides a storage medium for making a computer automatically execute the procedures of the evaluation method of a semiconductor layer.

A first storage medium according to the present invention is a storage medium used for estimating a physical quantity of a semiconductor layer based on at least the spectrum of cosΔ in accordance with a variation in the wavelength of measurement light after a process of holding the temperature of the semiconductor layer at a predetermined temperature higher than room temperature has been conducted. The amorphous region is located in the semiconductor layer in a substrate. The crystallinity of the amorphous region has been disordered by the implantation of dopant ions into the substrate. The measurement light has been incident on the semiconductor layer at an angle tilted relative to p and s directions in a plane vertical to the optical axis thereof and then reflected as an elliptically-polarized ray from the semiconductor layer. The p direction is defined by an intersection between the plane vertical to the optical axis and a plane containing incident and reflected rays. The s direction is vertical to the p direction in the plane vertical to the optical axis. Δ is a phase difference between p and s components as to the reflected ray. The storage medium stores a program for making a computer execute the procedures of: i) storing a correlation between the thickness of the amorphous region and at least the spectrum of cosΔ; ii) inputting at least the spectrum of the cosΔ as a measurement result obtained by a spectroscopic ellipsometry performed on the amorphous region formed on specific implant conditions; and iii) fetching the correlation and determining the thickness of the amorphous region in the semiconductor layer by reference to the correlation about at least the spectrum of cosΔ obtained in the step ii).

In the procedure i), a relationship between implant energy and the thickness of the amorphous region and a relationship between the spectrum of cosΔ and implant energy are stored as first and second correlations, respectively, with regard to each particular ion implant dose. And in the procedure iii), after the implant energy of the ions implanted into the semiconductor layer has been obtained by reference to the second correlation about the spectrum of cosΔ input in the procedure ii), the thickness of the amorphous region in the semiconductor layer can be determined by reference to the first correlation about the implant energy obtained.

Alternatively, in the procedure i), a relationship between an ion implant dose and the thickness of the amorphous region and a relationship between the spectrum of cosΔ and an ion implant dose are stored as first and second correlations, respectively, with regard to each particular implant energy. And in the procedure iii), after the implant dose of the ions implanted into the semiconductor layer has been obtained by reference to the second correlation about the spectrum of cosΔ input in the procedure ii), the thickness of the amorphous region in the semiconductor layer can be determined by reference to the first correlation about the ion implant dose obtained.

A second storage medium according to the present invention is a storage medium used for measuring a temperature of a heat treatment conducted on a semiconductor layer in a substrate based on at least the spectrum of cosΔ in accordance with a variation in the wavelength of measurement light. The semiconductor layer includes an amorphous region with crystallinity disordered by the implantation of dopant ions into the substrate. The measurement light has been incident on the semiconductor layer at an angle tilted relative to p and s directions in a plane vertical to the optical axis thereof and then reflected as an elliptically-polarized ray from the semiconductor layer. The p direction is defined by an intersection between the plane vertical to the optical axis and a plane containing incident and reflected rays. The s direction is vertical to the p direction in the plane vertical to the optical axis. Δ is a phase difference between p and s components as to the reflected ray. The storage medium stores a program for making a computer execute the procedures of: i) storing a relationship between a time of the heat treatment and a decrease in thickness of the amorphous region at a particular temperature as a correlation; ii) storing a thickness of the amorphous region prior to the heat treatment; iii) storing a thickness of the amorphous region posterior to the heat treatment; and iv) fetching the thicknesses of the amorphous region measured before and after the heat treatment is conducted and the correlation, and obtaining the temperature of the heat treatment by reference to the correlation about the decrease in thickness of the amorphous region before and after the heat treatment is conducted.

A third storage medium according to the present invention is a storage medium used for measuring a temperature of a heat treatment conducted on a semiconductor layer in a substrate based on at least the spectrum of cosΔ in accordance with a variation in the wavelength of measurement light. The semiconductor layer includes an amorphous region with crystallinity disordered by the implantation of dopant ions into the substrate. The measurement light has been incident on the semiconductor layer at an angle tilted relative to p and s directions in a plane vertical to the optical axis thereof and then reflected as an elliptically-polarized ray from the semiconductor layer. The p direction is defined by an intersection between the plane vertical to the optical axis and a plane containing incident and reflected rays. The s direction is vertical to the p direction in the plane vertical to the optical axis. $\Delta$ is a phase difference between p and s components as to the reflected ray. The storage medium stores a program for making a computer execute the procedures of: i) storing a recovery rate as a correlation for each particular temperature, the recovery rate being obtained based on a relationship between a time of the heat treatment and a decrease in thickness of the amorphous region at each said particular temperature; ii) storing a thickness of the amorphous region prior to the heat treatment; iii) storing a thickness of the amorphous region posterior to the heat treatment and a time of the heat treatment; and iv) fetching a decrease in thickness of the amorphous region before and after the heat treatment and the correlation, and obtaining the temperature of the heat treatment by reference to the correlation about the recovery rate obtained by dividing the decrease in thickness of the amorphous region before and after the heat treatment by the time of the heat treatment.

A fourth storage medium according to the present invention is a storage medium used for measuring a temperature of a heat treatment conducted on a semiconductor layer in a substrate based on at least the spectrum of $\cos\Delta$ in accordance with a variation in the wavelength of measurement light. The semiconductor layer includes an amorphous region with crystallinity disordered by the implantation of dopant ions into the substrate. The measurement light has been incident on the semiconductor layer at an angle tilted relative to p and s directions in a plane vertical to the optical axis thereof and then reflected as an elliptically-polarized ray from the semiconductor layer. The p direction is defined by an intersection between the plane vertical to the optical axis and a plane containing incident and reflected rays. The s direction is vertical to the p direction in the plane vertical to the optical axis. $\Delta$ is a phase difference between p and s components as to the reflected ray. The storage medium stores a program for making a computer execute the procedures of: i) storing a recovery rate as a correlation, the recovery rate being obtained based on a relationship between a temperature of the heat treatment and a decrease in thickness of the amorphous region at a particular time; ii) storing a thickness of the amorphous region prior to the heat treatment; iii) storing a thickness of the amorphous region posterior to the heat treatment and a time of the heat treatment; and iv) fetching a decrease in thickness of the amorphous region before and after the heat treatment and the correlation, and obtaining the temperature of the heat treatment by reference to the correlation about the recovery rate obtained by dividing the decrease in thickness of the amorphous region before and after the heat treatment by the time of the heat treatment.

BRIEF DESCRIPTION OF DRAWINGS

FIG. 2 is a diagram schematically showing the arrangement of an evaluation apparatus used for the evaluation in the embodiment of the present invention.

FIG. 7 is a graph illustrating in comparison the relationships between ion implant energy and the thickness of an amorphous region obtained by respective measurements according to TEM, TRIM and spectroscopic ellipsometry, as data in a first specific example.

FIG. 8 is a graph illustrating the relationship between an ion implant dose and the thickness of an amorphous region obtained by a measurement according to spectroscopic ellipsometry, as data in the first specific example of the first embodiment.

FIG. 16 is a graph illustrating the relationship between a temperature at which a wafer is held and the thickness of an amorphous region (amorphous region) in a wafer implanted with As$^+$ ions as data in a first specific example of the second embodiment.

FIG. 17 is a graph illustrating the relationship between a temperature at which a wafer is held and the film quality of an amorphous region (amorphous region) in a wafer implanted with As+ ions as data in a second specific example of the second embodiment.

FIG. 28 is a flowchart showing the procedure of deriving a temperature of a wafer surface based on a recovery rate during annealing conducted at a predetermined temperature in the second embodiment.

FIG. 29 is a flowchart showing the procedure of deriving a temperature of a wafer surface based on a recovery rate during annealing conducted for a predetermined period of time in the second embodiment.

FIG. 33 is a table drawn up to list the contents of the respective specific examples in the respective embodiments.

BEST MODE FOR CARRYING OUT THE INVENTION

FIG. 33 is a table drawn up to list the contents of the respective specific examples in the respective embodiments described below.

First, an evaluation method of a semiconductor for each embodiment supporting the basic principle of the invention will be described with reference to the drawings.

Figure 1:
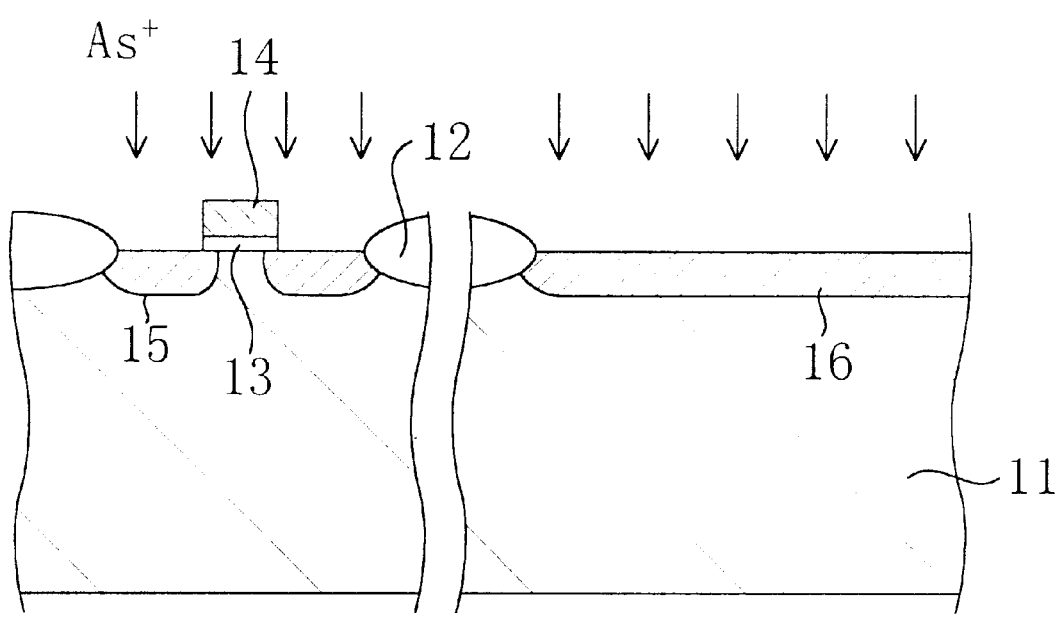
FIG. 1 is a cross-sectional view illustrating the structure of part of a semiconductor wafer used for evaluation in an embodiment of the present invention.

FIG. 1 is a cross-sectional view illustrating the structure of a semiconductor device (an n-channel MOS transistor), to be evaluated in the embodiment of the present invention, in an ion implantation step. As shown in FIG. 1, in the fabrication process performed on an MOS transistor in a wafer state, an element isolation 12 is formed out of a LOCOS film on a silicon substrate (silicon wafer) 11. And a gate insulating film 13 and a gate electrode 14 are formed in an active region surrounded with the element isolation 12. In the ion implantation step, dopant ions such as As+ ions are implanted into the silicon substrate 11, whereby high-concentration source/drain regions 15 of the n-channel MOS transistor are formed. In another region of the silicon substrate 11, a monitor region 16, used, for example, for determining whether or not conditions for implanting dopant ions at a high level are appropriate, is formed. And the As+ ions are also implanted into the monitor region 16 simultaneously with the source/drain regions 15. In forming source/drain regions for a p-channel MOS transistor, conditions for implanting boron ions are determined with B+ ions implanted into another monitor region.

FIG. 2 is a side view schematically illustrating the arrangement of a spectroscopic ellipsometer for determining the ion implantation conditions for the source/drain regions 15 of the n-channel MOS transistor by utilizing the monitor region 16. Xe light, output from a Xe light source 20, is transformed into linearly-polarized light by a polarizer 21, and then made to be incident on the silicon substrate 11 (the monitor region 16) at an angle $\theta_0$ with respect to a normal crossing the surface of the substrate at right angles. Light reflected as an elliptically-polarized ray is passed through an analyzer 23 and then made to be incident on a spectroscope 23. In this manner, a complex refractive index N=n−ik is measured at each wavelength by a detector 24 while analyzing the spectrum thereof. It is noted that the axis of the incident linearly-polarized light is tilted relative to a p direction (defined by an intersection between a plane vertical to the optical axis and a plane containing incident and reflected rays) and to an s direction (vertical to the p direction in the plane vertical to the optical axis).

Next, the principle of measurement according to the spectroscopic ellipsometry used in this embodiment will be described. Suppose the angle formed between the Xe incident light on the silicon substrate 11 and a normal crossing the silicon substrate at right angles in FIG. 2 is $\theta_0$, then the complex refractive index N=n−ik of a sample at each wavelength is represented by the following Equations (1) and (2):

$$n^2 - k^2 = \sin^2\theta_0 [1 + \{\tan^2\theta_0(\cos^2 2\psi - \sin^2 2\psi \sin^2\Delta)\}/(1+\sin 2\psi \cos\Delta)^2] \quad (1)$$

$$2nk = (\sin^2\theta_0 \tan^2\theta_0 \sin 4\psi \sin\Delta)/(1+\sin 2\psi \cos\Delta)^2 \quad (2)$$

where ψ is a ratio between the amplitude reflection factors of p and s components, and Δ is a phase difference between the p and s components. Specifically, the complex refractive index N representing the physical properties of a sample at each wavelength can be obtained by deriving $\tan\psi$ and $\cos\Delta$ of the reflected light based on the Equations (1) and (2).

The present inventors found during the following process that significant information on ion implantation conditions can be obtained by measuring and analyzing the spectra of $\tan\psi$ and $\cos\Delta$ of the reflected light without deriving the complex refractive index N itself of a sample.

In obtaining data shown in the diagrams referred to below, a p-type silicon substrate, already doped with a p-type dopant, is used as the silicon substrate, the resistivity of the substrate is in the range from 10.0 to 15.0 ($\Omega\cdot$cm) and the crystallographic orientation of the surface of the substrate is (100). Furthermore, $As^+$ is used as implanted ion species, with implant energy varied in the range from 20 to 80 kev and a dose varied in the range from 2 to $4\times10^{15}$ $cm^{-2}$. Also, the spectrometric analysis is conducted in the range from 250 to 800 nm.

Figure 3A:
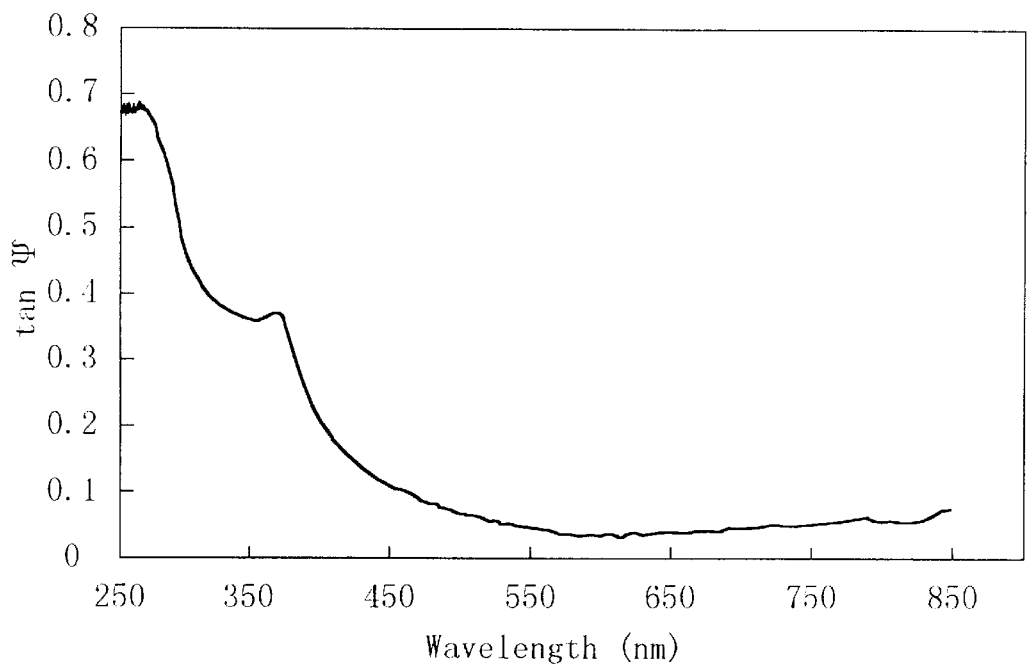
FIGS. 3(a) and 3(b) are graphs illustrating the spectra of $\cos\psi$ and $\cos\Delta$ in a low-concentration amorphous region, respectively, as data obtained by an experiment carried out in the embodiment of the present invention.
Figure 3B:
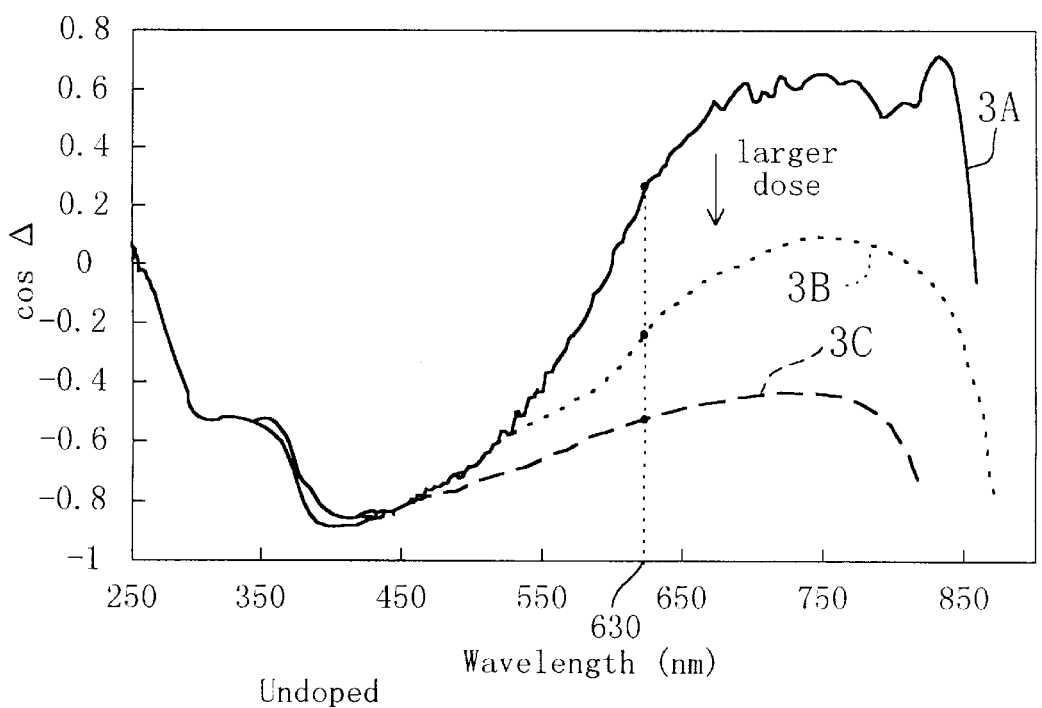
Figure 4A:
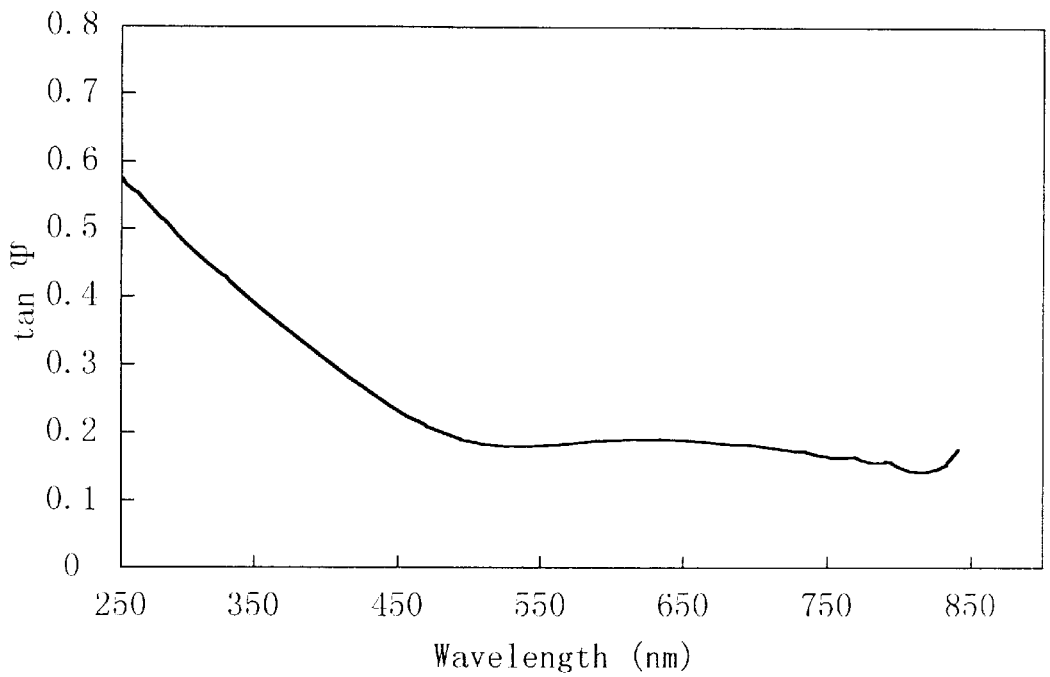
FIGS. 4(a) and 4(b) are graphs illustrating the spectra of $\cos\psi$ and $\cos\Delta$ in a high-concentration amorphous region, respectively, as data obtained by an experiment carried out in the embodiment of the present invention.
Figure 4B:
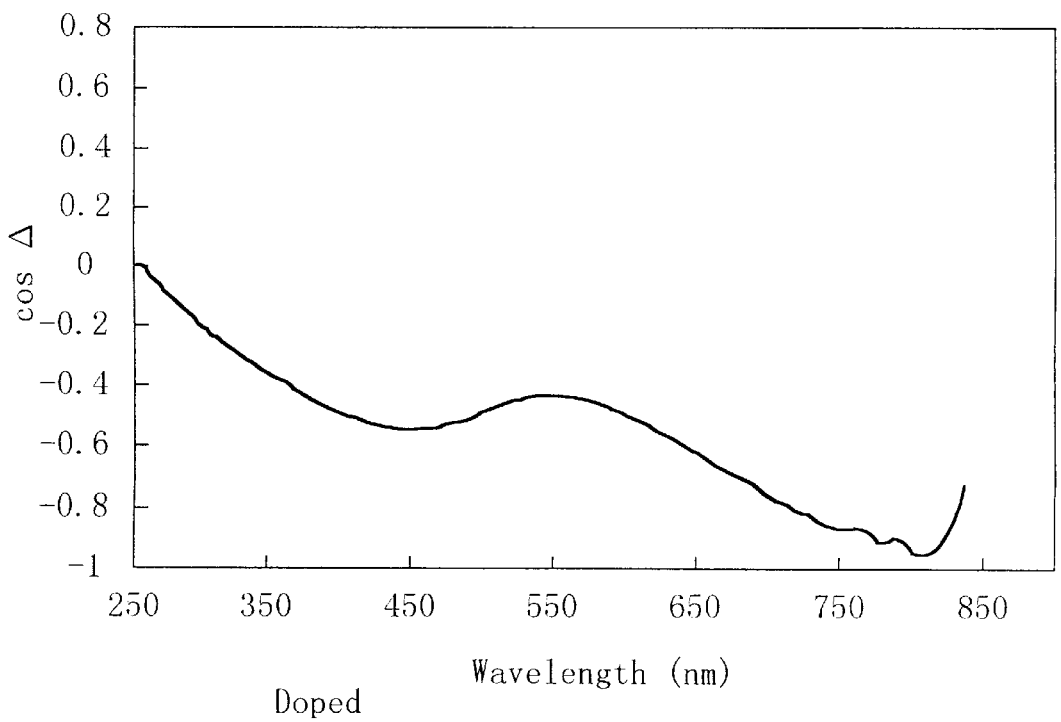

FIGS. 3(a) and 3(b) respectively illustrate the spectra of $\tan\psi$ and $\cos\Delta$ of the rays reflected from a silicon substrate implanted with no ions yet (shown as a spectral line 3A in FIG. 3(b)). FIGS. 4(a) and 4(b) respectively illustrate the spectra of $\tan\psi$ and $\cos\Delta$ of the rays reflected from a silicon substrate implanted with dopant ions at a high level. As can be understood by comparing the spectral line of $\cos\Delta$ having a valley at a wavelength of 450 nm in FIG. 4(b) with the spectral line 3A of $\cos\Delta$ having a valley at a wavelength of 400 nm in FIG. 3(b), when silicon single crystals are doped with a dopant, the shape of the spectrum of $\cos\Delta$ is transformed, so that the valley tends to be located in a longer-wavelength region (in the range from 450 nm to about 850 nm), and corresponds to a smaller negative value. Therefore, it is clear that the spectra of $\tan\psi$ and $\cos\Delta$ are changed by the ion implantation.

Furthermore, in general, as shown in FIG. 3(b), once the silicon single crystals are doped with a dopant, as the dose is increased, the spectrum of $\cos\Delta$ tends to shift from the spectral line 3A, corresponding to the non-implantation, toward the negative domain (spectral lines 3B and 3C) to reach a smaller value. Accordingly, by obtaining $\tan\psi$ and $\cos\Delta$ at a given wavelength (e.g., 630 nm) for a single crystalline silicon substrate, the conditions for the ion implantation such as a dose can be estimated to a certain degree.

Figure 5:
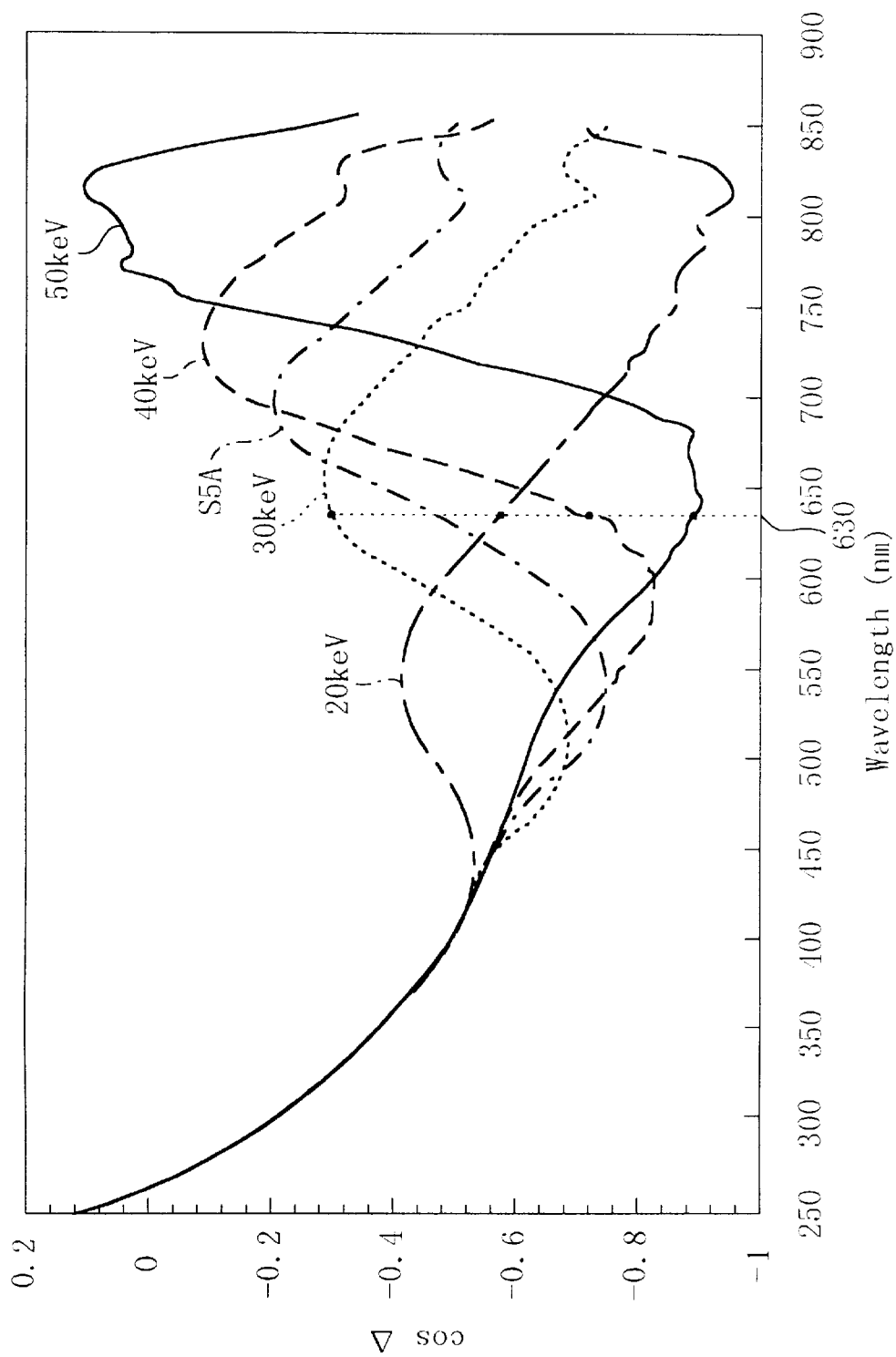
FIG. 5 is a graph illustrating the spectra of $\cos\Delta$ in an amorphous region implanted with ions at a high level with the implant energy thereof varied, as data obtained by an experiment carried out in the embodiment of the present invention.
Figure 6:
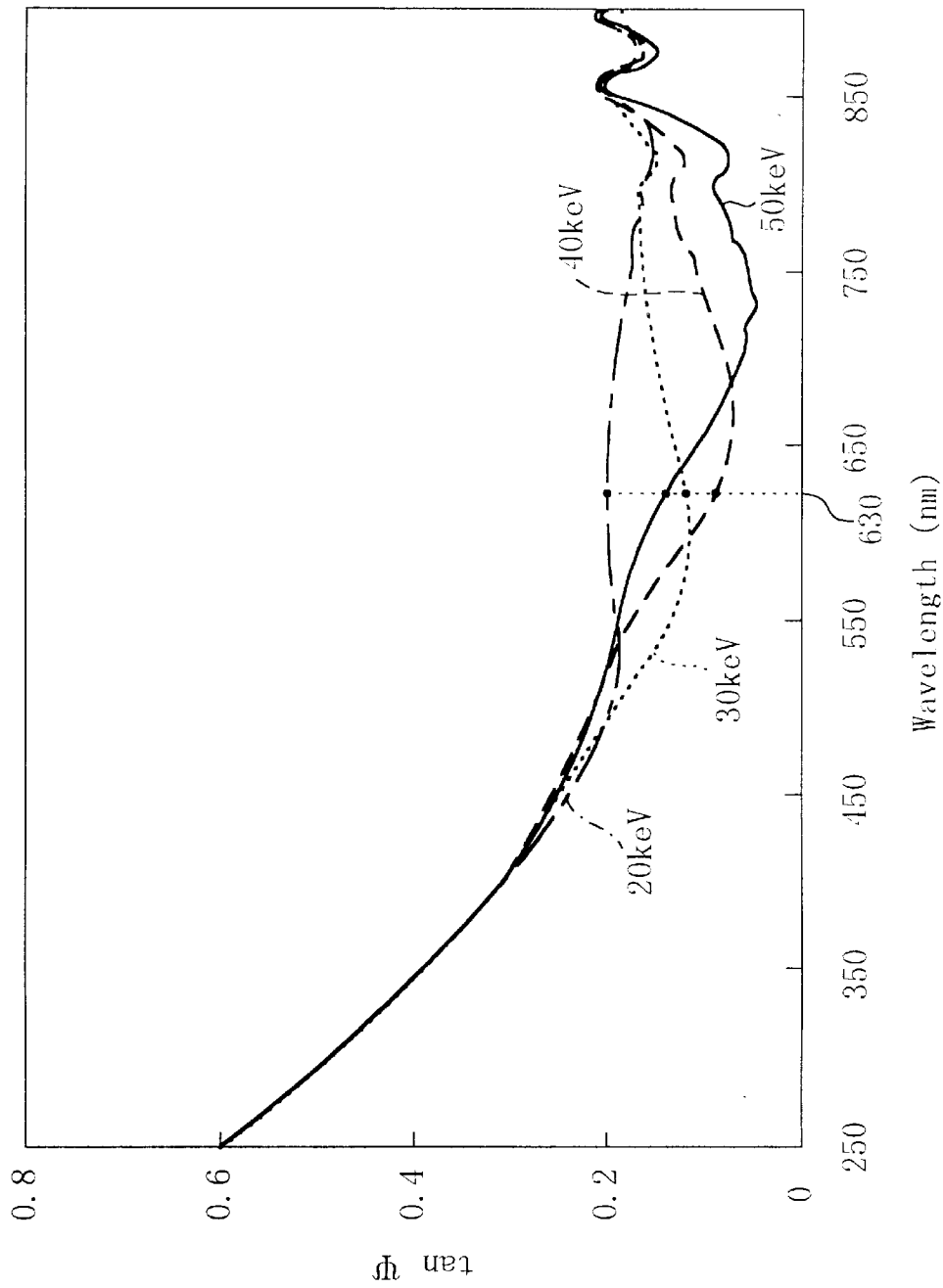
FIG. 6 is a graph illustrating the spectra of $\tan\psi$ in an amorphous region implanted with ions at a high level with the implant energy thereof varied, as data obtained by an experiment carried out in the embodiment of the present invention.

FIG. 5 illustrates the change of the spectral shapes of $\cos\Delta$ in accordance with the variation in the implant energy for an amorphous silicon layer, and FIG. 6 illustrates the change of the spectral shapes of $\tan\psi$ in accordance with the variation in the implant energy for an amorphous silicon layer. The dose of dopant ions ($As^+$) is $4\times10^{15}$ $cm^{-2}$.

As can be understood from FIGS. 5 and 6, in implanting ions into an amorphous silicon layer, the ion implant energy cannot be derived from these measurement results even if $\tan\psi$ and $\cos\Delta$ are obtained at a given wavelength (e.g., 630 nm), because there is no regularity in the variation of the values of $\tan\psi$ and $\cos\Delta$ in accordance with the increase of the implant energy.

As described above, in accordance with the conventional technique, it is impossible to determine by the ellipsometry whether or not the conditions such as ion implant energy are appropriate as to an impurity diffusion region formed by implanting dopant ions at a high level.

EMBODIMENT 1

Hereinafter, specific examples will be described as exemplary information obtained by the spectroscopic ellipsometry.

Specific Example 1

In this specific example, a method of determining the thickness of an amorphous region (or an "ion implanted region", so to speak) by reference to a correlation about the spectrum of $\cos\Delta$ (or $\tan\psi$) obtained by the spectroscopic ellipsometry will be described. In this specification and claims, a "spectrum" may be understood as a spectral pattern or as (a table of) values of $\cos\Delta$ (or $\tan\psi$) relative to wavelengths.

In obtaining data shown in FIGS. 7 and 8, a p-type silicon substrate, already doped with a p-type dopant, is used as the silicon substrate, the resistivity thereof is in the range from 10.0 to 15.0 ($\Omega\cdot$cm) and the crystallographic orientation of the surface of the substrate is (100). Furthermore, $As^+$ is used as implanted ion species, with implant energy varied in the range from 20 to 80 keV and a dose varied in the range from 2 to $4\times10^{15}$ $cm^{-2}$. The spectrometric analysis is conducted in the range from 250 to 800 nm.

Figure 20B:
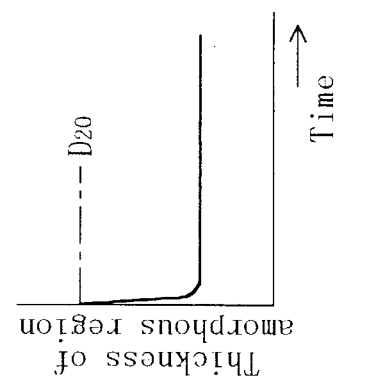
FIG. 20(b) is a graph illustrating a variation in the thickness of an amorphous region with the passage of time where ordinary annealing is performed on the conditions for point D20 of FIG. 20(a)
Figure 20A:
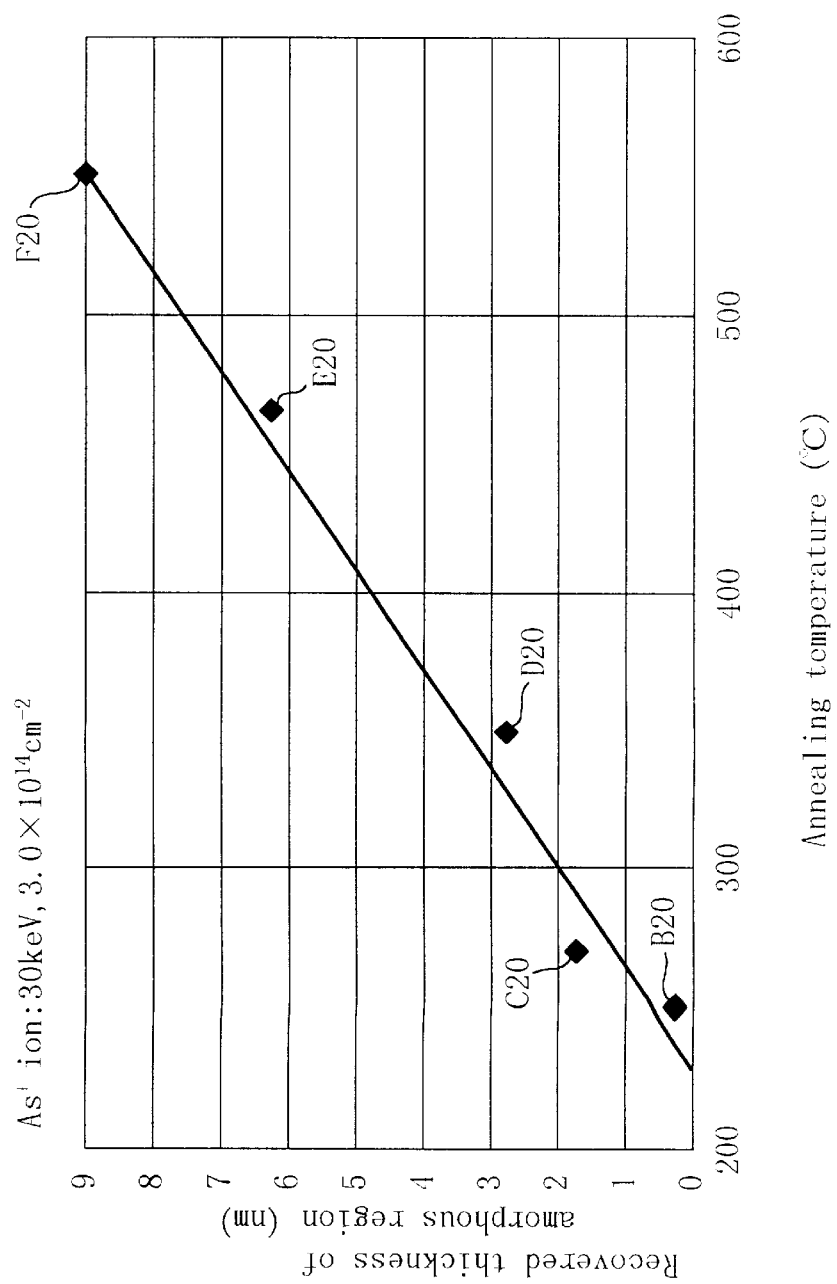
FIG. 20(a) illustrates data illustrating the temperature dependence of a decrease in thickness of an amorphous region (amorphous region) in accordance with flash annealing in a fourth specific example of the second embodiment.

FIG. 7 illustrates data representing the dependence of the thickness of an amorphous region on the implant energy where the implant dose is held at a constant value of $4\times10^{15}$ $cm^{-2}$. In FIG. 7, the axis of abscissas indicates the implant energy (keV) and the axis of ordinates indicates the thickness of the amorphous region (nm). The data shown in FIG. 7 is obtained by measuring the thicknesses of amorphous regions for the implant energy conditions shown in FIGS. 5 and 6 (i.e., 20, 30, 40 and 50 kev) in accordance with TEM and by finding correlations between the resultant spectral shapes of $\cos\Delta$ and $\tan\psi$ and the measured thicknesses of the amorphous regions. FIG. 7 also shows the relationship between the implant energy and the thickness of an amorphous region obtained in accordance with TEM. As can be understood FIG. 7, the thickness of the amorphous region obtained by the spectroscopic ellipsometry of this embodiment approximates the thickness actually measured with TEM, and thus, precise measurement can be performed nondestructively. In other words, an evaluation method suitable for an in-line test (which is a test carried out between processes as shown in FIG. 20) can be provided.

FIG. 8 shows data representing the dependence of the thickness of an amorphous region on the implant dose where the ion implant energy is held at a constant value of 40 keV. In FIG. 8, the axis of abscissas indicates the implant dose ($\times10^{15}$ $cm^{-2}$) and the axis of ordinates indicates the thickness of an amorphous region (nm). The data of FIG. 8 is obtained by measuring the thicknesses of amorphous regions in accordance with TEM with the implanted dose (dose) varied at five steps of 2.0, 2.5, 3.0, 3.5 and $4.0\times10^{15}$ $cm^{-2}$, and by finding correlations between the spectral shapes of $\cos\Delta$ and $\tan\psi$ and the measured thicknesses of the amorphous regions.

Figures 30A, 30B:
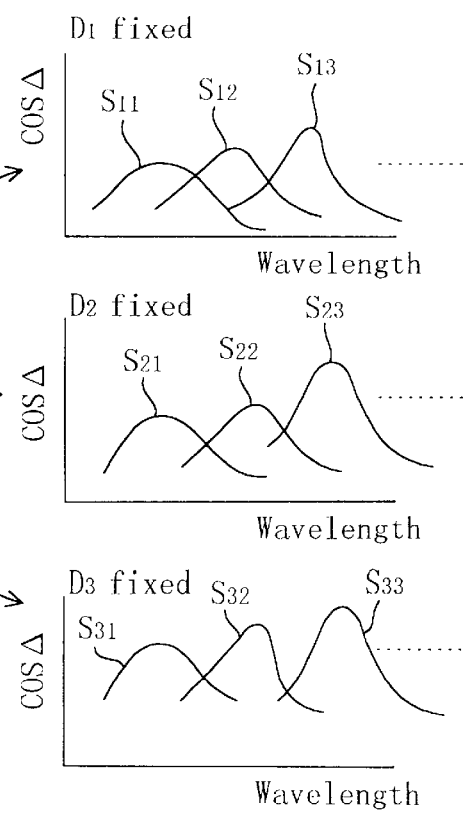
FIGS. 30(a) and 30(b) are tables respectively showing first and second correlations in the first specific example of the first embodiment.

FIG. 30(a) is a matrix in which the thicknesses d11, d12, d13, etc. of amorphous regions, each obtained with the implant dose D fixed and the implant energy E varied at values E1, E2, E3, etc., are correlated with various implant doses D1, D2, D3, etc. The relationship between the implant energy E and the thickness d of an amorphous region, shown in this matrix and obtained with the ion implant dose fixed, will be regarded as a first correlation. The first correlation can be represented as the dependence of the thickness of an amorphous region on the implant energy shown in FIG. 7.

Alternatively, the matrix shown in FIG. 30(a) may be regarded as a table in which the thicknesses d11, d21, d31, etc., each obtained with the implant energy E fixed and the implant dose D varied at values D1, D2, D3, etc., are correlated with implant energy values E1, E2, E3, etc. In such a case, the relationship between the implant dose D and the thickness d of an amorphous region, shown in this matrix and obtained with the ion implant energy fixed, is the first correlation. This first correlation can be represented as the dependence of the thickness of an amorphous region on the implant dose as shown in FIG. 8.

FIG. 30(b) is a matrix in which the spectral patterns of cosΔ (or a numerical relationship between a measurement wavelength and cosΔ), each obtained with the implant dose D fixed and the implant energy E varied at values E1, E2, E3, etc., are correlated with various implant doses D1, D2, D3, etc. The relationship shown in this matrix between the implant energy E and the spectrum of cosΔ will be regarded as a second correlation.

Alternatively, the matrix shown in FIG. 30(b) may be regarded as a table in which the spectra of cosΔ, each obtained with the implant energy E fixed and the implant dose varied at values D1, D2, D3, etc., are correlated with various implant energy values E1, E2, E3, etc. In such a case, the relationship between the implant energy and the spectrum of cosΔ, shown in this matrix and obtained at a constant implant dose D, is regarded as the second correlation.

In this specific example, by using the data shown in FIGS. 5, 7, 8, 30(a) and 30(b), the thickness of an amorphous region can be obtained by the following methods.

In a first method, which is the simplest, the spectral pattern of cosΔ (or tan ψ) (or a numerical relationship between a measurement wavelength and cosΔ), obtained by performing a measurement on an amorphous region in accordance with the spectroscopic ellipsometry, is referred to the relationships between cosΔ (or tan ψ) and wavelengths on various implantation conditions shown in FIG. 30(b) (i.e., the second correlation), thereby choosing the most matched one and determining the thickness of the amorphous region. In this method, either the spectral shape or the table of correspondence between the wavelength values and the values of cos Δ may be used. In accordance with this method, attention is focused on the point that, once ions implanted are determined, a unique spectral shape of cosΔ (or tan ψ) can be obtained from an implant dose or energy. When the spectral shape is used, a fingerprint identification system may be applied, for example.

Figure 31:
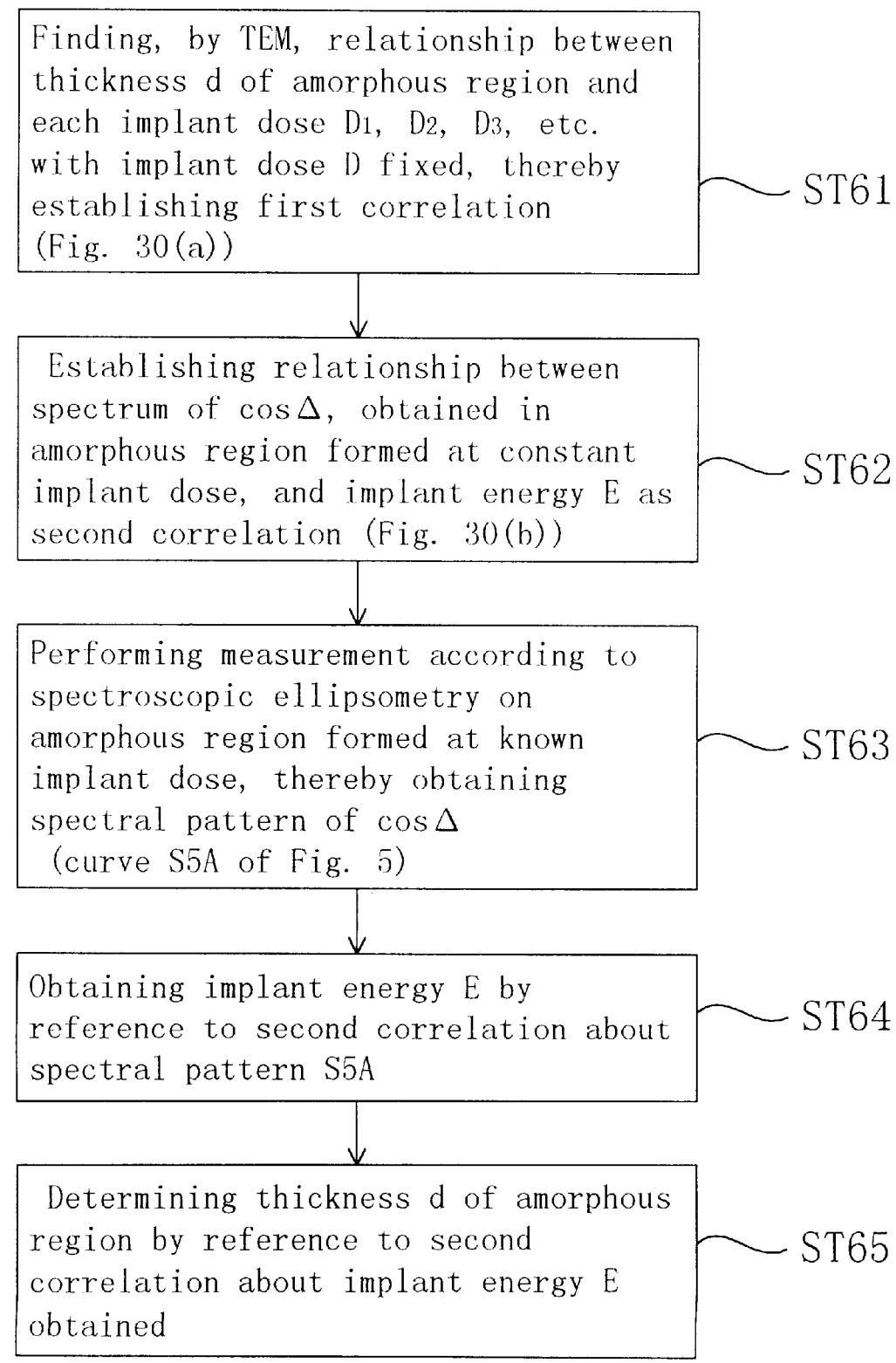
FIG. 31 shows a method for obtaining the thickness of an amorphous region by utilizing the first and second correlations where an ion implantation dose is given in the first specific example of the first embodiment.

In a second method, which is shown in FIG. 31, the thickness of an amorphous region is obtained by utilizing the first and second correlations when an implant dose for the ion implantation is known.

First, in Step ST61, the thicknesses d of amorphous regions, each obtained with the implant dose D fixed and the implant energy E varied at values E1, E2, E3, etc., are derived in accordance with TEM for each of various implant doses D1, D2, D3, etc. These relationships are stored as the first correlations shown in FIG. 30(a).

Next, in Step ST62, the relationships between the spectra of cosΔ, obtained from an amorphous region formed at a constant implant dose, and the implant energy E are established and stored as the second correlation shown in FIG. 30(b).

Then, in Step ST63, the spectral pattern of cosΔ is obtained by performing a measurement according to the spectroscopic ellipsometry on an amorphous region formed at a known implant dose. A table of correspondence between the wavelength values and the value of cosΔ may be drawn up instead. For example, suppose a spectral pattern SA5 shown in FIG. 5 is herein obtained.

Next, in Step ST64, the spectral pattern SA5 is referred to the second correlation, thereby obtaining the implant energy E. In the example shown in FIG. 5, the implant energy E resulting in the spectral pattern SA5 is assumed to be 35 keV, for example.

Then, in Step ST65, the implant energy E obtained is referred to the first correlation, thereby determining the thickness d of the amorphous region. For example, if the implant energy E has been turned out to be 35 keV, the thickness of the amorphous region can be determined as 62 nm by reference to the table of FIG. 30(b) or FIG. 7. In general, the thickness of an amorphous region may be defined by approximately every 5 nm, and this thickness of the amorphous region may be approximated at 60 nm. In practice, if arrangements are made so that the thickness can be calculated based on the data actually measured by the ellipsometry as shown in FIG. 7, the thickness of an amorphous region can be calculated instantaneously by this method through computation based on the measured data within an apparatus in the same manner as in the first method. It is clear that the result of calculation substantially accords with the value actually measured by TEM.

Figure 32:
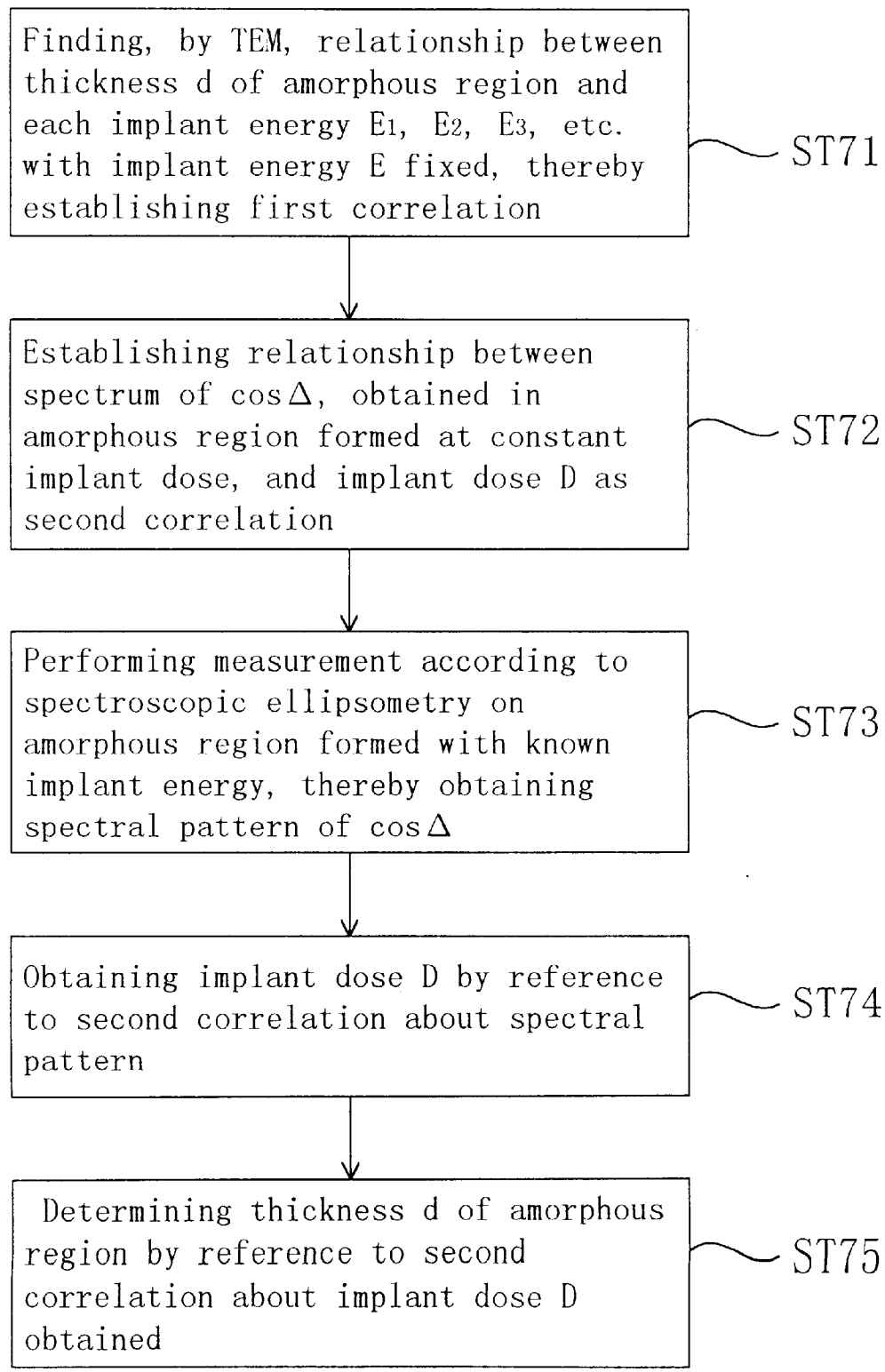
FIG. 32 shows a method for obtaining the thickness of an amorphous region by utilizing the first and second correlations where ion implant energy is given in the first specific example of the first embodiment.

In a third method, which is shown in FIG. 32, the thickness of an amorphous region is obtained by using the first and second correlations when implant energy for the ion implantation is known.

First, in Step ST71, the thicknesses d of amorphous regions, each obtained with the implant energy E fixed and the implant dose varied at values D1, D2, D3, etc., are derived in accordance with TEM for each of various implant energy values E1, E2, E3, etc. These relationships are stored as the first correlations.

Next, in Step ST72, the relationships between the spectra of cosΔ, obtained from an amorphous region formed at constant implant energy, and the implant dose are drawn up and stored as the second correlation shown in FIG. 30(b).

Then, in Step ST73, the spectral pattern of cosΔ is obtained by performing a measurement according to the spectroscopic ellipsometry on an amorphous region formed at known implant energy. A table of correspondence between the wavelength values and the value of cosΔ may be drawn up instead.

Next, in Step ST74, the spectral pattern of cosΔ is referred to the second correlation, thereby obtaining the implant dose D.

Then, in Step ST75, the implant dose D obtained is referred to the first correlation, thereby determining the thickness d of the amorphous region. That is to say, the thickness of the amorphous region can be determined by reference to the table of FIG. 30(b) or FIG. 8. In practice, if arrangements are made so that the thickness can be calculated based on the data actually measured by the ellipsometry as shown in FIG. 8, the thickness of an amorphous region can be calculated instantaneously by this method through computation based on the measured data within an apparatus in the same manner as in the first method.

In a fourth method, the dependence of the thickness of an amorphous region on the implant energy shown in FIG. 7 is combined with the relationship between the implant energy and the spectral shape shown in FIG. 5. In a predetermined wavelength region in the spectrum of cosΔ of the reflected light, the thickness of an amorphous region can be substantially estimated if the wavelength corresponding to a local maximum of the spectrum is known. If the first correlation is established in the same manner as in the second method and if the relationship between the wavelength corresponding to the local maximum and the implant energy E is stored as the second correlation for each ion implant dose, the thickness of an amorphous region can be obtained with ease through a similar procedure to that of the flowchart shown in FIG. 31.

In a fifth method, the dependence of the thickness of an amorphous region on the implant dose shown in FIG. 8 is combined with the relationship between the implant dose and the spectral pattern shown in FIG. 3(b). In a predetermined wavelength region in the spectrum of cosΔ of the reflected light, the thickness of an amorphous region can be substantially estimated if the wavelength corresponding to a local maximum of cosΔ in the spectrum is known. If the first correlation is established in the same manner as in the third method and if the relationship between the local maximum of cosΔ and the implant energy E is stored as the second correlation for each ion energy, the thickness of an amorphous region can be obtained with ease through a similar procedure to that of the flowchart shown in FIG. 32.

Specific Example 2

(In-Plane Distribution of Thicknesses of Amorphous Regions)

Figure 9C:
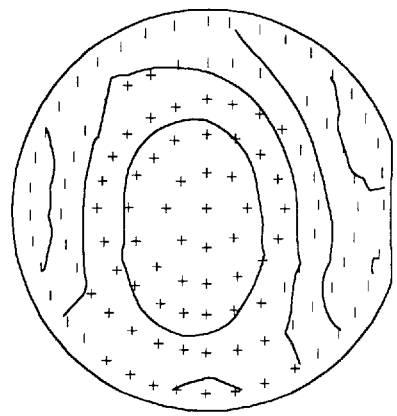
FIGS. 9(a) through 9(c) are diagrams for comparing the in-wafer uniformity of the thickness of an amorphous region obtained by a measurement according to spectroscopic ellipsometry as data of a second specific example of the first embodiment with data on the in-wafer uniformity obtained according to thermal wave and sheet resistance methods.
Figure 9B:
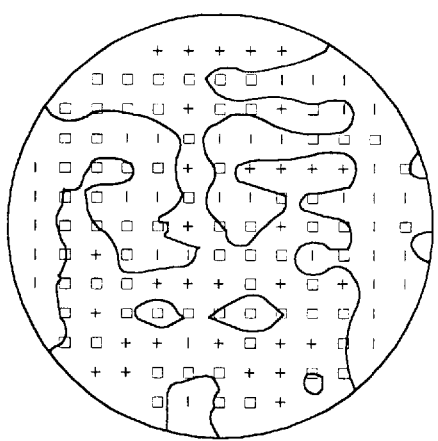
Figure 9A:
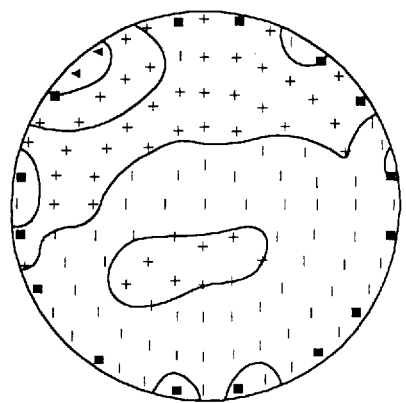

FIGS. 9(a), 9(b) and 9(c) are diagrams illustrating the in-wafer-plane uniformities of amorphous regions obtained by performing measurements according to spectroscopic ellipsometry, thermal wave method and sheet resistance method, respectively, on the same wafer. These diagrams show results of measurement on the conditions that As$^+$ is implanted at implant energy of 40 keV and an implant dose of $5 \times 10^{15}$ cm$^{-2}$. In accordance with the spectroscopic ellipsometry according to this embodiment shown in FIG. 9(a), the thickness of the amorphous region is 69 nm and the in-plane uniformity is 0.153%. In FIG. 9(a), a portion shown with symbols (–) having a reduced thickness corresponds to the amorphous region. FIG. 9(b) shows the in-plane uniformity of an ion implant dose in accordance with the thermal wave method, in which a portion shown with symbols (□) corresponds to a region with an average value. FIG. 9(c) shows the in-plane uniformity of an ion implant dose in accordance with the sheet resistance method. In each of these drawings, a contour line corresponds to a boundary between areas with a difference of 0.5%. Herein, a value obtained by the thermal wave method is merely a relative quantity, and it cannot be determined whether or not the value accurately accords with the ion implant dose. In the data shown in FIG. 9(c), the in-plane uniformity of the ion implant dose is very poor. When the sheet resistance measurement is employed, a heat treatment is required for activating the implanted impurity in order to measure the sheet resistance, and it seems that the in-plane uniformity has been degraded through this heat treatment.

In contrast, although the method for measuring the in-plane uniformity of the thickness of an amorphous region by spectroscopic ellipsometry of this embodiment is nondestructive, variation in thickness of the amorphous region in the wafer plane can be analyzed as a variation resulting from implantation conditions alone, not involved with a factor concerning a heat treatment.

Specific Example 3

The present specific example relates to information derived from the characteristic shapes of spectral lines of tan ψ and cosΔ measured by the spectroscopic ellipsometry of this invention.

Figure 10:
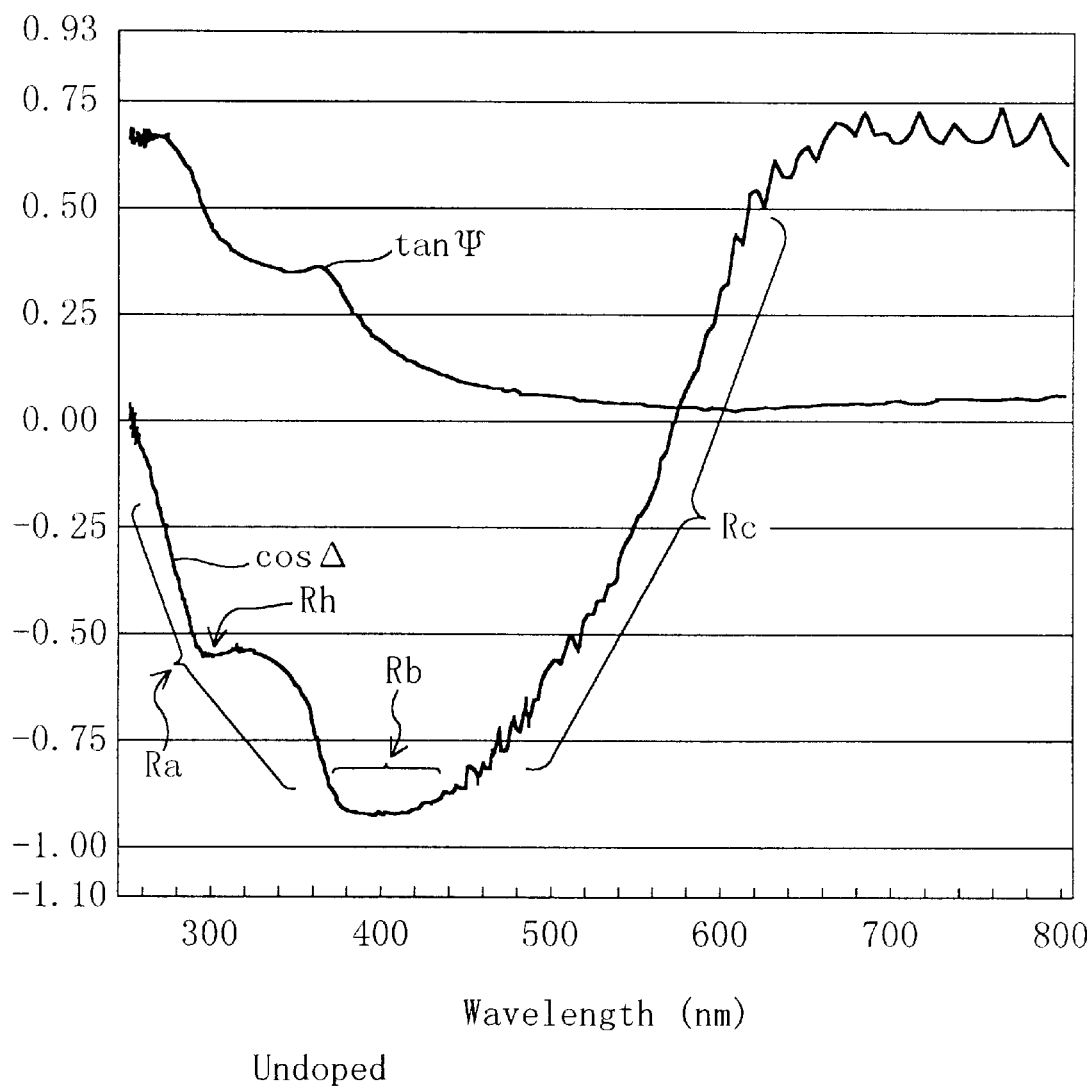
FIG. 10 illustrates the spectra of $\cos\Delta$ and $\tan\psi$ in a single crystalline silicon region where no ion has been implanted, as control data in a third specific example of the first embodiment.

FIG. 10 shows the spectral lines of tan ψ and cosΔ obtained by performing the spectroscopic ellipsometry on a silicon substrate not implanted with dopant ions. FIGS. 11 through 15 show the spectral lines of tan ψ and cosΔ obtained by performing the spectroscopic ellipsometry on regions in silicon substrates implanted with dopant ions on respective conditions shown in these drawings.

The spectral line of cosΔ of FIG. 10 for the silicon substrate not implanted with a dopant includes three characteristic regions Ra, Rb and Rc. The region Ra is a decreasing region where the spectral line changes diagonally down to the right. The region Rb is a local minimum region having a certain width where the value of cosΔ reaches a local minimum. The region Rc is an increasing region where the spectral line changes diagonally up to the right. Also, the decreasing region Ra is characterized by a hump portion Rh. By comparing the shapes of these characteristic regions in the respective diagrams with the shapes of the spectral lines of cosΔ and tan ψ obtained by the spectroscopic ellipsometry after the ion implantation, the following information are obtained:

(1) Difference in the shape of spectral line owing to difference in dose:

The relationship between a difference in implant dose and a difference in the spectral shape of cosΔ obtained by using the same implanter will now be discussed. Comparing FIGS. 11 and 12 with each other, the gradient of the spectral line of cosΔ in the decreasing region Ra is gentler in FIG. 11, and the hump portion Rh to be observed in the decreasing region Ra is more indistinct in FIG. 11. While the hump portion Rh distinctly appears in the spectral line of cosΔ of the undoped substrate as shown in FIG. 10, the hump portion Rh does not distinctly appear in FIG. 11. This means that an amorphous region can be formed in a silicon substrate more easily on the conditions of FIG. 11, i.e., when the implant dose of dopant ions is larger. Similarly, comparing FIGS. 13 and 14 with each other, the gradient in the decreasing region Ra is gentler and the hump portion Rh is more indistinct in FIG. 14 using the conditions with a larger ion implant dose, and thus, the same conclusion can be derived.

Figure 12:
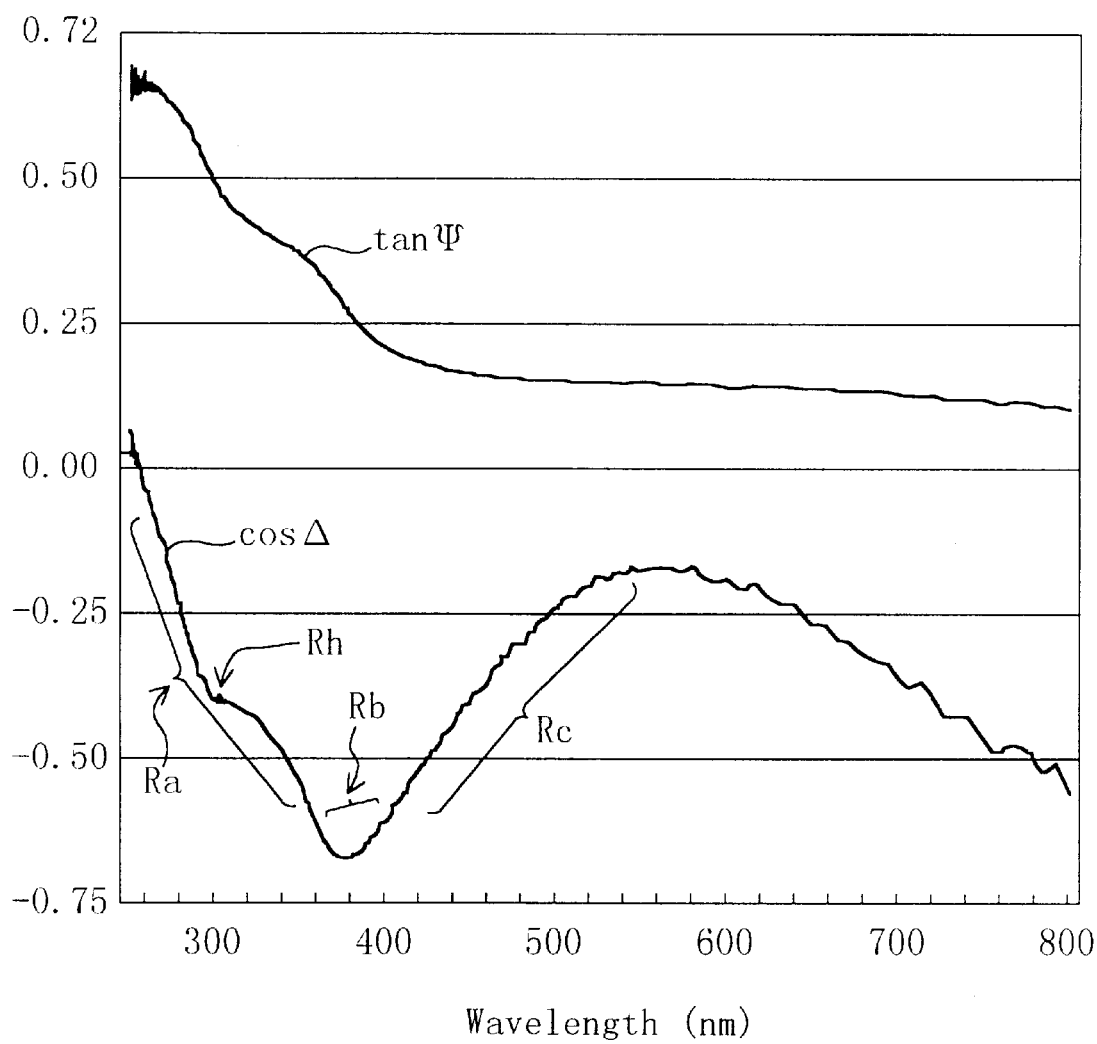
FIG. 12 illustrates the spectra of $\cos\Delta$ and $\tan\psi$ in an amorphous region implanted with ions at $5\times10^{13}$ cm$^{-2}$ using the ion implanter manufactured by the company A, as data in the third specific example of the first embodiment.
Figure 13:
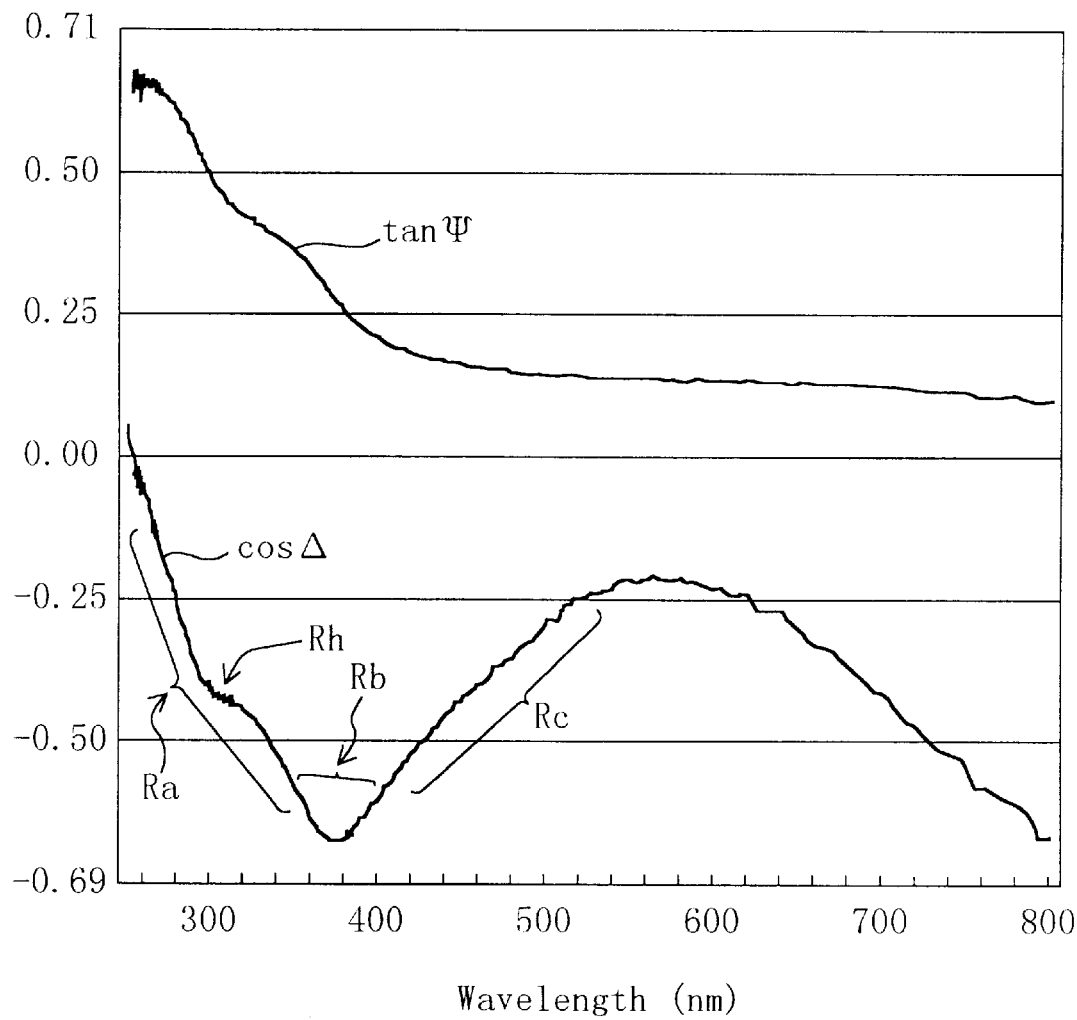
FIG. 13 illustrates the spectra of $\cos\Delta$ and $\tan\psi$ in an amorphous region implanted with ions at $5\times10^{13}$ cm$^{-2}$ using an ion implanter manufactured by company B, as data in the third specific example of the first embodiment.

(2) Comparison between the performances of implanters:

Comparing FIGS. 12 and 13 with each other, the hump portion Rh of the spectral line in the decreasing region Ra is more indistinct and the gradient in the increasing region Rc is gentler in FIG. 13. As shown in FIG. 10, in the spectral line of cosΔ of the undoped substrate, the hump portion Rh appears more distinctly and the gradient in the increasing region Rc is steeper. Since the ion implantation conditions for FIGS. 12 and 13 are the same except for the types of implanters, it can be understood that an amorphous region can be more easily formed in a silicon substrate by the ion implanter manufactured by company B. In other words, in accordance with the method of this embodiment, the performance of an ion implanter can be evaluated.

Figure 14:
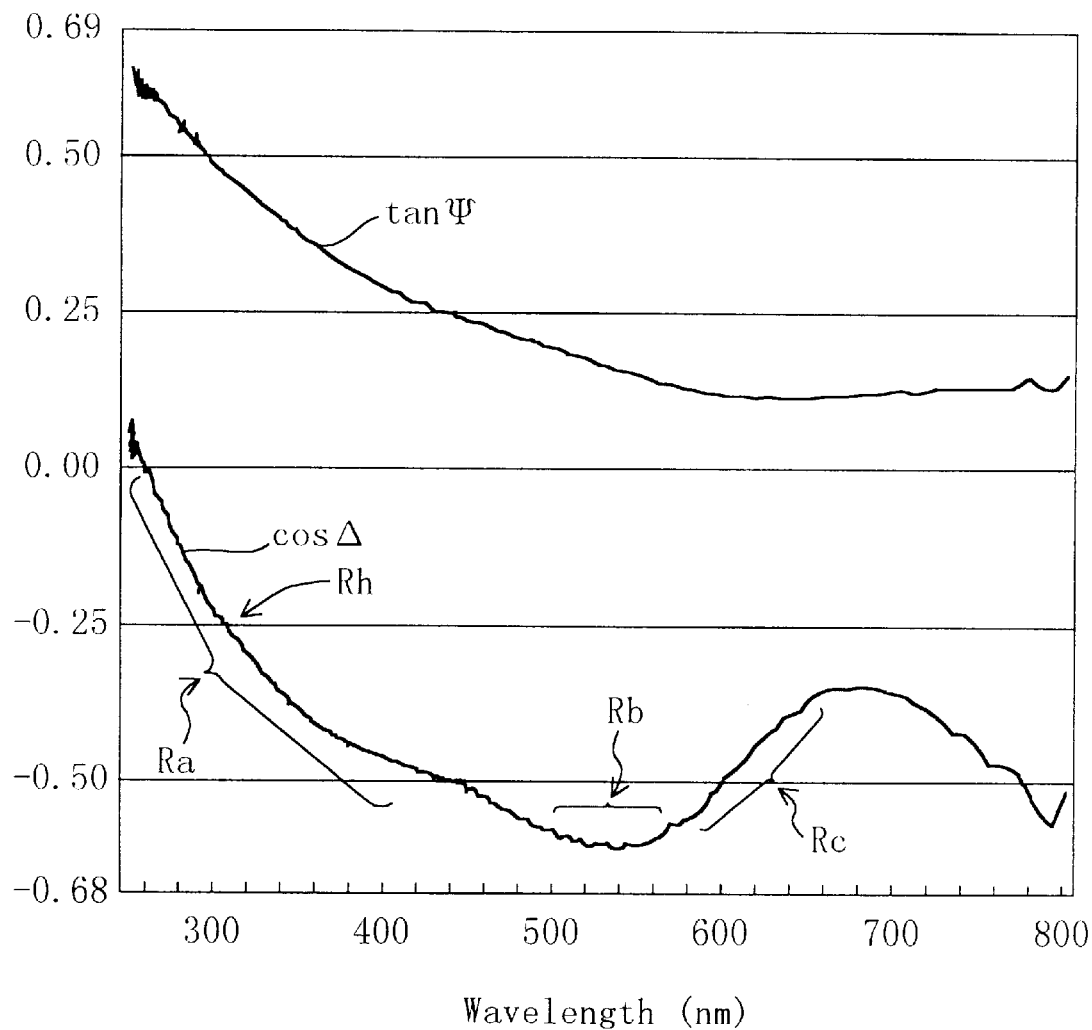
FIG. 14 illustrates the spectra of $\cos\Delta$ and $\tan\psi$ in an amorphous region implanted with ions at $1\times10^{14}$ cm$^{-2}$ and a current density of 615 $\mu$A using the ion implanter manufactured by the company B, as data in the third specific example of the first embodiment.
Figure 15:
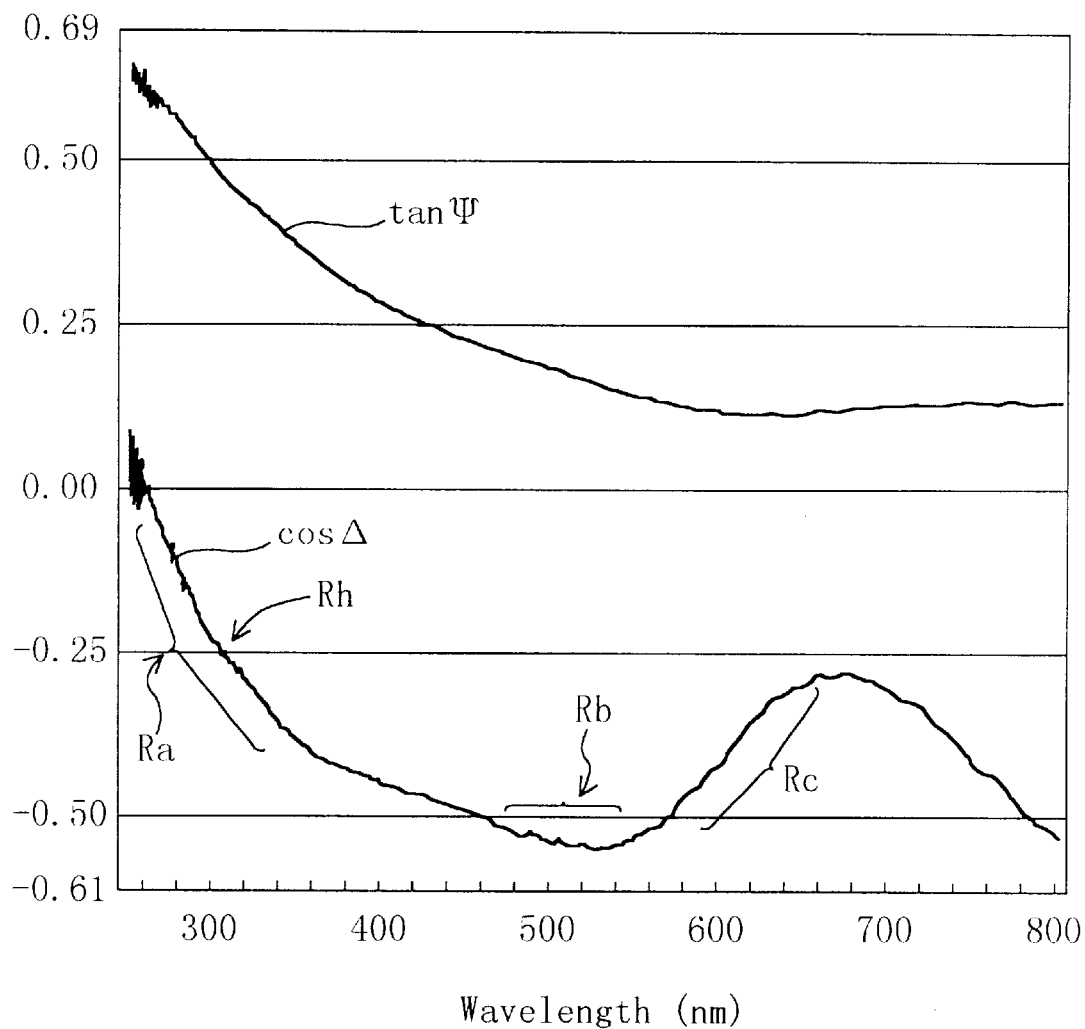
FIG. 15 illustrates the spectra of $\cos\Delta$ and $\tan\psi$ in an amorphous region implanted with ions at $1\times10^{14}$ cm$^{-2}$ and a current density of 2000 $\mu$A using the ion implanter manufactured by the company B, as data in the third specific example of the first embodiment.

(3) Current density dependency:

Comparing FIGS. 14 and 15 with each other, the gradients of the spectral line in the decreasing and increasing regions Ra, Rc are slightly gentler in FIG. 14 than in FIG. 15. This can be understood because, for example, the value of cosΔ at the wavelength of 300 nm in FIG. 14 is smaller than the value of cosΔ at the same wavelength in FIG. 15. Accordingly, an amorphous region is less likely to be formed in a silicon substrate on the conditions for FIG. 15. Comparing the conditions for FIGS. 14 and 15 with each other, the only difference therebetween is that a current density is larger in the conditions for FIG. 15. Specifically, if the ion implantation is performed with large current as in FIG. 15, a so-called beam anneal effect in which an amorphous region tries to recover its crystallinity in response to the ion implantation is generated.

Figure 11:
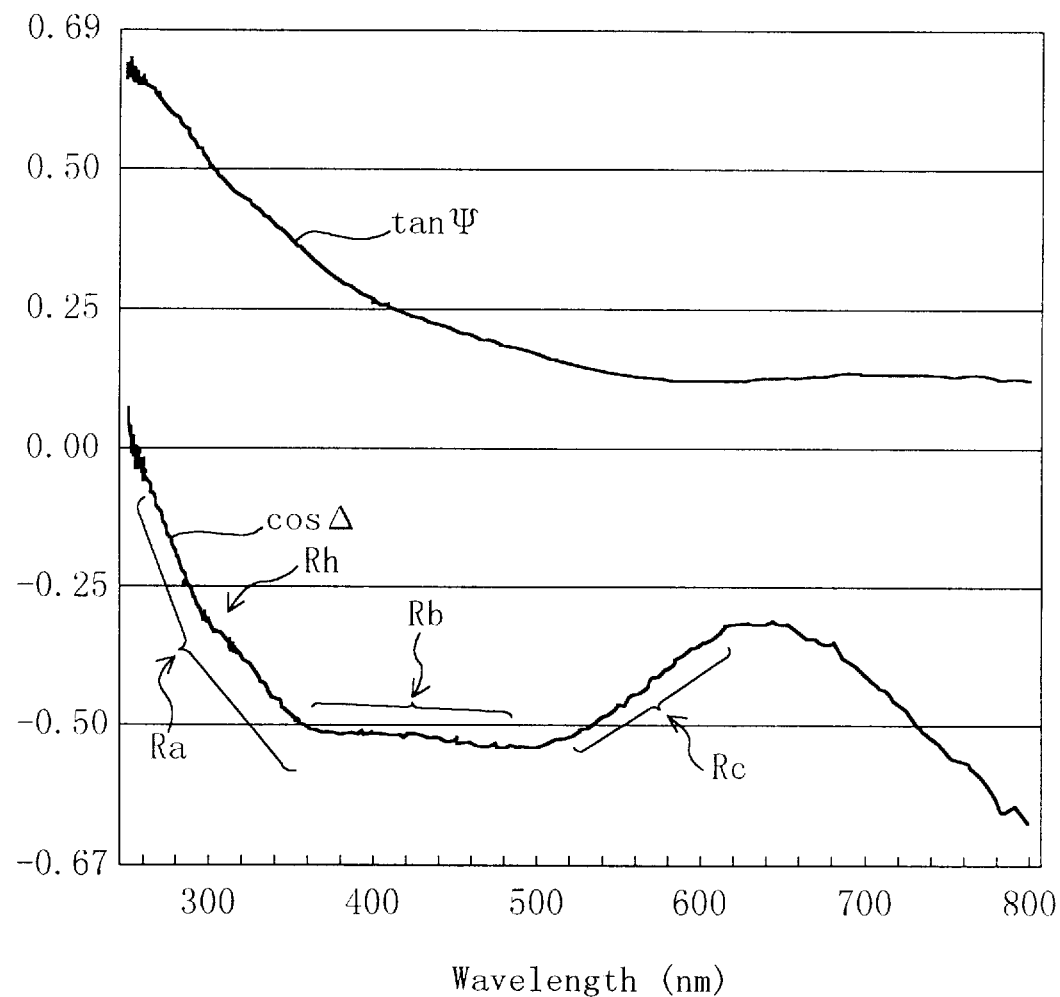
FIG. 11 illustrates the spectra of $\cos\Delta$ and $\tan\psi$ in an amorphous region implanted with ions at $1\times10^{14}$ cm$^{-2}$ using an ion implanter manufactured by company A, as data in the third specific example of the first embodiment.

Comparing FIGS. 11 and 15 with each other about this current density dependency, although these spectra are both obtained at the same ion implant dose, the hump portion Rh is more distinct and the gradient in the decreasing region Ra is slightly steeper in FIG. 11 than in FIG. 15. Furthermore, the local minimum region Rb is flat in FIG. 11, where the amorphous region has a smaller thickness. These results tell that the ion implanter of company A exhibits greater beam anneal effect than the ion implanter of company B using the implantation conditions with a current density of 2000 $\mu$A. It is noted that the current density of the ion implanter of company A is unknown.

(4) Other information:

For example, comparing FIGS. 10, 11 and 12 with one another, it can be understood that the crystallinity is disordered to a larger degree (more amorphous) as the spectral shape of tan $\psi$ is gentler. Accordingly, taking the spectral shape of tan $\psi$ into consideration as well as the spectral shape of cos$\Delta$, the ion implantation conditions and the physical quantity of an amorphous region can be more accurately determined than considering only the spectral shape of cos$\Delta$. However, since the spectral pattern of cos$\Delta$ includes a larger number of characteristic regions and is varied to a larger degree depending upon the ion implantation conditions, it is generally sufficient to observe the spectral pattern of cos$\Delta$ alone.

In each of the aforementioned specific examples, As$^+$ ions are implanted as the dopant ions. However, the present invention is not limited to these specific examples. Alternatively, this invention is applicable to a semiconductor layer to which B$^+$ ions, Si$^+$ ions, P$^+$ ions or the like have been implanted. Furthermore, the semiconductor layer is not necessarily a silicon layer, but may be a semiconductor layer made of any other semiconductor material such as a compound semiconductor.

EMBODIMENT 2

Next, the second embodiment, relating to the application of spectroscopic ellipsometry to the measurement of an actual temperature on a substrate surface during a process such as annealing, will be described.

Specific Example 1

(Method for Measuring Actual Temperature on Substrate Surface)

First, the relationship between an annealing process and the thickness of an amorphous region is obtained.

FIG. 16 shows data illustrating the relationship between the temperature at which a wafer is held and the thickness of an amorphous region where As$^+$ ions have been implanted into the wafer at 30 keV and $3\times10^{14}$ cm$^{-2}$. The axis of abscissas indicates the power of the power supply of a degassing chamber, which is 0% in OFF State and 100% at the maximum. The degassing chamber is a chamber attached to a CVD system or a sputtering system, and a wafer is heated and retained in vacuum in the degassing chamber. The power of the degassing chamber is indicated as 0 through 100% in this manner, but the surface temperature of the substrate placed in the chamber cannot be accurately known. The axis of ordinates indicates the thickness of an amorphous region measured after a sample has been retained at a predetermined temperature. A wafer including a semiconductor layer to which As$^+$ ions have been implanted and a degassing chamber for pre-heating provided to a Ti sputtering system are used, and the substrate is heated in vacuum in the chamber. Also, the thickness of the amorphous region is measured in the same manner as described with reference to FIGS. 7 and 8. Specifically, the thicknesses of an amorphous region are measured on the conditions corresponding to points A16, B16 and C16 by performing the spectroscopic ellipsometry on the amorphous region. The amorphous region is retained in the degassing chamber for 30 sec. in each case, and a so-called TC wafer, provided with a temperature sensor on its back surface, is used for measuring the temperature. However, with the TC wafer, only the temperature on the back surface of the wafer can be measured and the temperature on the top surface thereof cannot be known. The point A16 in FIG. 16 corresponds to a state where the wafer has been retained in the degassing chamber for the time of "0", i.e., the data about an "as-implanted" sample. The point B16 corresponds to the data obtained when the power supplied to the degassing chamber reaches 40% of the rated power (the temperature on the back surface measured on the TC wafer is 250° C.) The point C16 corresponds to the data obtained when the power supplied to the degassing chamber reaches 60% of the rated power (the temperature on the back surface is 270° C.). And the point D16 corresponds to the data obtained when the power supplied to the degassing chamber reaches 70% of the rated power (the temperature on the back surface is 350° C.). When annealing is conducted at such a low temperature, the thickness does not change so much but does decrease in 30 sec.

Figure 19:
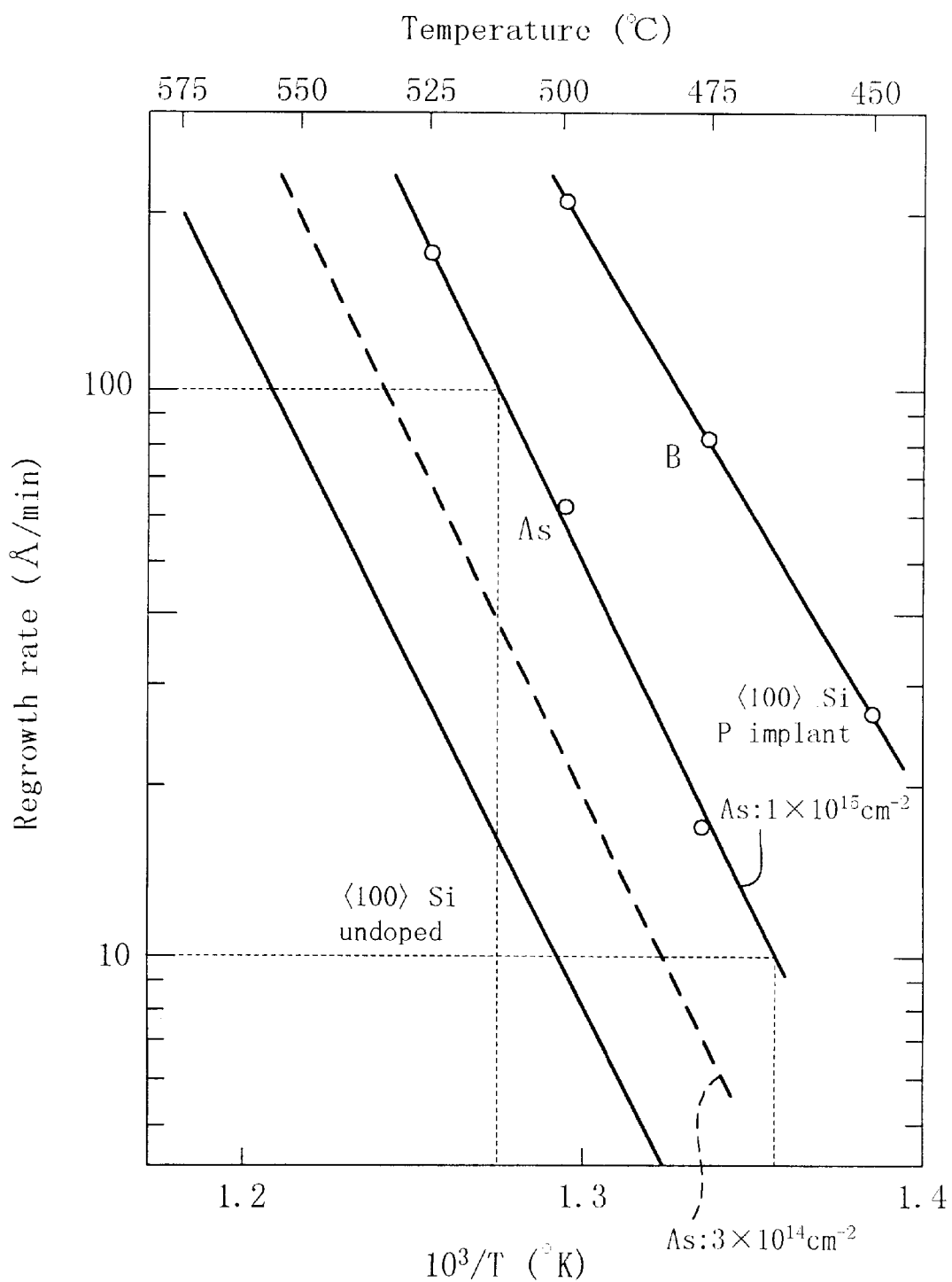
FIG. 19 is a graph illustrating the relationship between a rate at which recovery (recrystallization) proceeds in an amorphous region and an annealing condition described in a literature.

FIG. 19 corresponds to FIG. 4 described in a literature (Journal of Applied Physics Vol. 48, No. 10, October 1977, p. 4237), illustrating the relationship between a recovery (recrystallization) rate of an amorphous region and an annealing condition. In FIG. 19, the axis of abscissas indicates the temperature, and the axis of ordinates indicates the rate of recovery from amorphous state to crystalline state. As can be understood from this diagram, the recovery rate of an amorphous region formed by implanting, for example, As ions is approximately 60 Å/min. at 500° C. As shown in FIG. 19, it is known that there is a definite correlation between the annealing temperature and the recovery. However, no data is provided for the recovery rate at a temperature equal to or lower than 450° C.

In an amorphous region formed by implanting, for example, As$^+$ ions at $1\times10^{15}$ cm$^{-2}$, it has been considered that the amorphous region does not recover (or is recrystallized) if the annealing temperature is equal to or lower than approximately 450° C. On the other hand, according to the data shown in FIG. 16, a decrease in thickness of the amorphous region is observed even if the annealing is conducted at as low a temperature as about 250° C. to about 350° C., and hence, it was confirmed that an amorphous region recovers (or is recrystallized) to some degree even at such a low temperature.

Conventionally, the temperature within a chamber is measured with a temperature sensor provided on the back surface of a TC wafer. However, although the temperature on the back surface of a wafer can be sensed using a TC wafer, the temperature on the top surface of the wafer, i.e., the actual temperature at which an amorphous region is subjected to the heat treatment cannot be measured. Also, the range of the temperatures measurable with a TC wafer is limited, and it is said that the measurement accuracy is degraded when the temperature reaches a certain high point (in the range from 500 to 600° C. or more).

In contrast, according to the method of this specific example, the temperature on the top surface of a wafer can be precisely measured by using the correlation between the holding time and the recovery rate or between the holding time and a decrease in thickness to be used in the specific examples described below. Accordingly, even in an apparatus in which merely a percentage of the power supplied is indicated as in the degassing chamber, the surface temperature of a wafer associated with particular power supplied can be accurately measured. The surface temperature of a wafer cannot be known based on the experiment data alone. But if the thicknesses before and after the heat treatment are known by using the thickness measurement described in the first embodiment, the temperature during the heat treatment can be estimated based on the correlation between the holding time and the recovery rate or between the holding time and a decrease in thickness. Specific methods thereof will be described later.

In this specific example, the measurement of the temperature on the top surface of a wafer placed in a degassing chamber has been described. Alternatively, the temperature on the top surface of a wafer can also be accurately measured in a similar manner in any other apparatus such as a CVD system, a sputtering system and an annealing system. Furthermore, since the temperature on the top surface of a wafer can be measured, the distribution of temperatures in a wafer plane or in a region where the wafer is placed within the chamber can be also sensed.

Specific Example 2

Next, the results of an experiment performed in a second specific example for finding the relationship between an annealing condition and the film quality of an amorphous region (amorphous region) will be described.

FIG. 17 shows data illustrating the relationship between the temperature at which a wafer is held and the absorption coefficient of light incident on an amorphous region. In FIG. 17, the conditions of the wafer, the retaining time in the degassing chamber and the like are the same as those adopted in measuring the thickness shown in FIG. 16. A point A17 in FIG. 17 corresponds to the data in the state where the wafer has been retained in the degassing chamber for the time of "0", i.e., the data about an "as-implanted" sample. A point B17 corresponds to the data obtained when the power supplied to the degassing chamber reaches 40% of the rated power (the back surface temperature is 250° C.). A point C17 corresponds to the data obtained when the power supplied to the degassing chamber reaches 60% of the rated power (the back surface temperature is 270° C.). And a point D17 corresponds to the data obtained when the power supplied to the degassing chamber reaches 70% of the rated power (the back surface temperature is 350° C.). In FIG. 17, each parenthesized temperature is the temperature measured with a temperature sensor attached to a TC wafer. The absorption coefficient does not change so much but to a certain degree in 30 sec.

It was found from the results of the experiment shown in FIG. 17 that a difference in the film quality of an amorphous region depending on an annealing condition can also be estimated. Although it takes a certain time to observe spectral shapes obtained by the spectroscopic ellipsometry, if the absorption coefficient alone is to be obtained, the film quality can be evaluated very quickly and easily. The absorption coefficient depends upon the transparency of an amorphous region and reflects the crystallographic state of an amorphous region. Accordingly, a range of absorption coefficients, which is not likely to result in defective products, may be defined and prepared beforehand as an appropriate range during a fabrication process. Then, it can be determined very rapidly during an actual fabrication process whether or not a product is acceptable. Specifically, if the absorption coefficient of an amorphous region is within the appropriate range, then the resulting product will be acceptable. Alternatively, if the absorption coefficient is out of the appropriate range, then the resulting product will be defective.

Specific Example 3

Next, a third specific example, relating to the correlation between variations in the thickness and absorption coefficient of an amorphous region (amorphous region) during annealing and a holding time obtained by measuring the thickness in accordance with the spectroscopic ellipsometry, will be described.

Figures 18A, 18B:
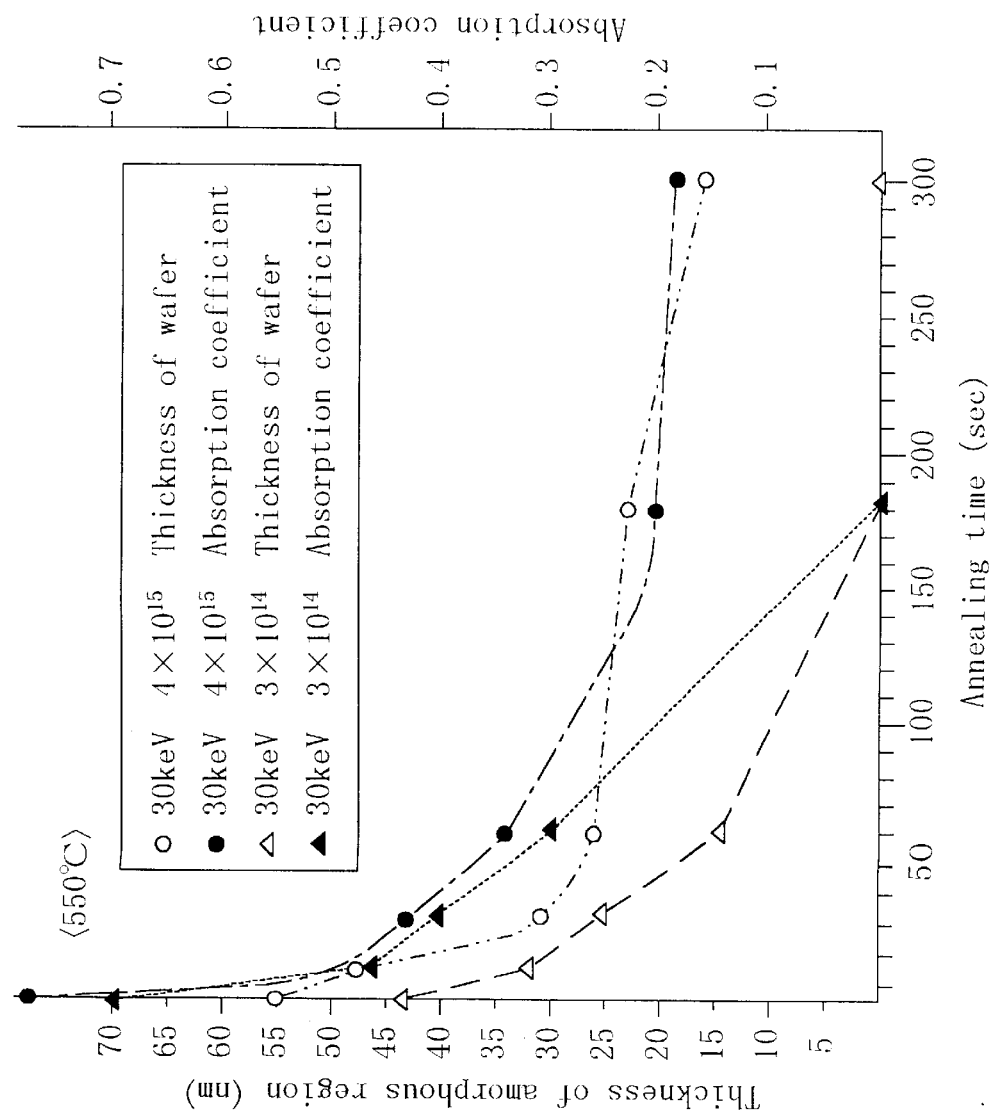
FIG. 18(a) is a graph illustrating a variation in the thickness of an amorphous region with respect to an annealing time for various samples as data in a third specific example of the second embodiment.
FIG. 18(b) is a table drawn up from the data of FIG. 18(a)

FIG. 18($a$) shows data illustrating variations in thickness and absorption coefficient with an annealing time for various samples. In FIG. 18($a$), the variation in thickness of a wafer, to which ions have been implanted at 30 keV and $4 \times 10^{15}$ cm$^{-2}$, is represented with ○, the variation in absorption coefficient of a wafer, to which the ions have been implanted under the same condition, is represented with ●, the variation in thickness of a wafer, to which the ions have been implanted at 30 keV and $3 \times 10^{14}$ cm$^{-2}$, is represented with Δ, and the variation in absorption coefficient of a wafer, to which the ions have been implanted under the same condition, is represented with ▲. All the samples are held at a temperature of 550° C. for a predetermined period of time.

Based on the gradients of the lines respectively linking the data shown with ○ and Δ, the following observations can be made.

With regard to the data shown with Δ, the variation in thickness from the start of annealing until 10 seconds have passed is (44.8–32) nm/10 sec.=77 nm/min. This recovery (recrystallization) rate is much larger than the recovery rate of 20 nm/min. at a temperature of 550° C. (corresponding to a point X) shown in FIG. 19. The recovery rate in 50 seconds from a point in time 10 seconds have passed since the start of the annealing until a point in time 60 seconds have passed is (32−15) nm/50 sec.=17 nm/50 sec.=20.4 /min. This value is substantially equal to the recovery rate of 20 nm/min. at 550° C. shown in FIG. 19. The recovery rate in 120 seconds from a point in time 60 seconds have passed until a point in time 180 seconds have passed is 15/120 (sec.)=7.5 nm/min., which is very small. Thereafter, at a point in time 120 seconds have passed, the amorphous region has already disappeared.

With regard to the data shown with ○, the variation in recovery rate is substantially equal to that of the data shown with Δ. It should be noted, however, in an amorphous region formed by implanting low-concentration ions at a dose as low as $3 \times 10^{14}$ cm$^{-2}$, the recovery proceeds with the passage of annealing time and the thickness ultimately becomes substantially "0". In contrast, the thickness of an amorphous region formed by implanting high-concentration ions at a dose as high as $4 \times 10^{15}$ cm$^{-2}$ is substantially constant after 50 seconds have passed. In other words, after about 50 seconds have passed, the recovery hardly proceeds. This phenomenon probably has something to do with the amount of residual oxygen.

Furthermore, with regard to the data shown with ● and ▲, the variations are comparatively similar to those of the data shown with ○ and Δ. This means that not only the variation in film quality but also the variation in thickness can be analyzed to a certain degree by observing the values of the absorption coefficient.

FIG. 18(*b*) is a table in which the annealing time, the thickness of the amorphous region and the recovery rate obtained from the data shown in FIG. 18(*a*) (the annealing at 550° C.) are listed. This table is drawn up for the data shown with Δ, but a similar table can be drawn up for the data shown with ○. If a table such as that shown in FIG. 18(*b*) is prepared for each of various annealing temperatures, an annealing temperature can be determined based on the recovery rate and the holding time.

In this manner, according to this specific example, the variation in the rate of recovery from the amorphous state to the crystalline state with the passage of time can be obtained at a predetermined annealing temperature, and an annealing temperature can be also sensed.

Specific Example 4

Next, a fourth specific example for finding the relationship between the annealing temperature and the variation in thickness along with the recovery of an amorphous region (amorphous region), similar to the data shown in FIG. 19, during low-temperature annealing conducted at 550° C. or less, inter alia at 450° C. or less, will be described.

FIG. 20(*a*) shows the data illustrating the dependence of a recovery rate of an amorphous region on the temperature where flash annealing has been conducted with the holding time set at substantially "0". That is to say, annealing is conducted on a wafer under a condition where the power supply is turned off immediately after the temperature has increased. The data in FIG. 20(*a*) is obtained in a wafer implanted with As$^+$ ions at 30 keV and $3\times10^{14}$ cm$^{-2}$. As shown in FIG. 20(*a*), it can be seen that the decrease in thickness resulting from the recovery of the amorphous region varies substantially linearly with the annealing temperature. As for the recovery of an amorphous region (amorphous region) formed under the conditions shown in FIG. 20(*a*), the lower the annealing temperature is, the more remarkably the recovery tends to slow down, even if the annealing time is extended any more.

In FIG. 20(*a*), points B20, C20, D20, E20 and F20 respectively correspond to annealing at 250° C., 270° C., 350° C., 450° C. and 550° C. At these points, the recovery thicknesses of the amorphous region are 0.4 nm, 1.8 nm, 2.8 nm, 6.2 nm and 9 nm, respectively. At the three points B20, C20 and D20, the annealing temperature is so low that a unique phenomenon occurs in the recovery from the amorphous state to the crystalline state.

FIG. 20(*b*) is a graph illustrating the variation in thickness of an amorphous region with the passage of time where ordinary annealing is performed under the conditions of the point D20. As shown in FIG. 20(*b*), even if the amorphous region is retained for a long period of time under the conditions of the point D20 after the thickness thereof has decreased by 2.8 nm in a very short period of time, the crystallization does not proceed any longer and the thickness of the amorphous region remains constant. The similar phenomenon is observed during ordinary annealing under conditions of the points B20 and C20. Specifically, while the annealing temperature is low, the thickness of the amorphous region immediately decreases but the crystallization does not proceed thereafter. Suppose an amorphous region, formed by implanting, for example, As$^+$ ions at 30 keV and $3\times10^{14}$ cm$^{-2}$ is retained for a desired period of time in a system for conducting a process at a temperature equal to or lower than 450° C., at which the recovery from the amorphous state to the crystalline state is less likely to proceed, and the decrease in thickness of the amorphous region before and after the process is obtained. Then, the accurate annealing temperature can be estimated based on the data of FIG. 20(*a*) by utilizing this phenomenon.

If the data as shown in FIG. 20(*a*) is previously obtained for amorphous regions (specifically, such as source/drain regions in a MOSFET) formed under various ion implantation conditions, an annealing temperature can also be estimated in the low temperature annealing at 450° C. or lower based on the thicknesses of the amorphous regions measured by the ellipsometry. For example, under the conditions for flash annealing, if the thickness of the amorphous region has changed by about 6 nm before and after the annealing, the annealing temperature would be approximately 440° C.

Specifically, by utilizing such a measurement result, an actual annealing temperature can be estimated by reference to such data about actual thickness variation and processing conditions. Furthermore, based on such data, the annealing conditions can be set accurately.

Moreover, annealing may be conducted with constant heating power, and the correlation between the temperature and the thickness may be obtained by using the heating power as a parameter.

With regard to annealing conducted at a temperature of 450° C. or more for a comparatively short period of time, an annealing temperature can be estimated based on the recovery rate obtained from the decrease in thickness of an amorphous region measured with an ellipsometer and the annealing time by using the data shown in FIG. 19. However, the recovery state of an amorphous region is variable with the ion implantation conditions and the annealing temperatures as shown in FIG. 18. Accordingly, the data shown in FIG. 19 is not always suitable for accurate measurement of a temperature. Thus, it is preferred that the temperature dependence of the decrease in thickness of an amorphous region as shown in FIG. 20 is previously obtained for various ion implantation conditions. In particular, if the annealing time is variable, then it is preferably defined beforehand how the thickness of an amorphous region varies with the passage of annealing time as shown in FIG. 18.

Next, by utilizing the data described in the first through fourth specific examples, the temperature can be measured in the following manner.

Figure 27:
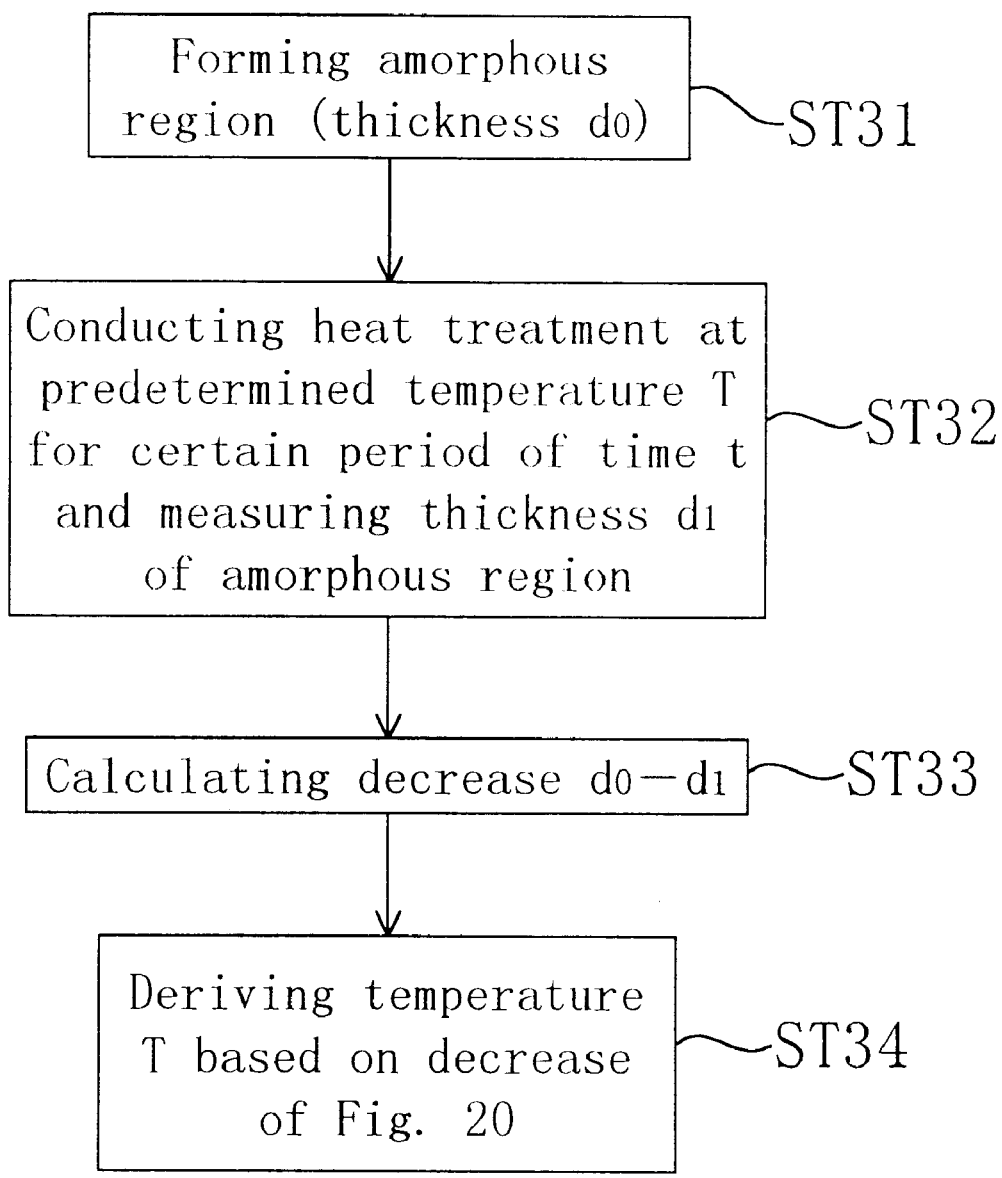
FIG. 27 is a flowchart showing the procedure of deriving a temperature of a wafer surface during annealing in the second embodiment.

FIG. 27 is a flowchart illustrating the procedure for determining a temperature on the surface of a wafer during annealing by utilizing the data of FIG. 20.

First, in Step ST31, an amorphous region with a thickness d0 is formed. Next, in Step ST32, a heat treatment (annealing) is conducted at a predetermined temperature T for a certain period of time t, and the resultant thickness d1 of the amorphous region is measured. Then, in Step ST33, the decrease d0−d1 in thickness of the amorphous region is calculated. Finally, in Step ST34, the calculated decrease is compared with the decrease shown in FIG. 20, thereby determining the predetermined temperature T.

FIG. 28 is a flowchart illustrating the procedure for determining the temperature on the surface of a wafer based on the recovery rate during annealing at a predetermined temperature by utilizing the data in FIG. 18.

First, in Step ST41, an amorphous region with a thickness d0 is formed. Next, in Step ST42, a heat treatment (annealing) is conducted at a predetermined temperature T with the given time t varied at t1, t2 and t3, and the resultant thicknesses d1, d2 and d3 of the amorphous region are measured. Then, in Step ST43, the recovery rates r (=d0−d1/t1, d0−d2/t2 and d0−d3/t3) of the amorphous region are calculated. Finally, in Step ST44, the recovery rate in FIG. 18 (or FIG. 19) is compared with the calculated recovery rates r, thereby determining the predetermined temperature T. Also, since the thickness at any point in times can be found in comparing the recovery rates, the annealing temperature can also be determined by utilizing FIG. 18(a) if the decrease in thickness of the amorphous region is known. For example, if the initial thickness is found 44.8 nm and the thickness after the annealing has been conducted for 10 seconds is found 32 nm as a result of the measurement, the annealing temperature can be determined at 550° C. with reference to the prepared data such as that shown in FIG. 18(a) about various annealing temperatures.

FIG. 29 is a flowchart illustrating the procedure for determining the temperature on the surface of a wafer based on a recovery rate during annealing conducted for a certain period of time by preparing the data such as that shown in FIG. 18 for various annealing temperatures.

First, in Step ST51, an amorphous region with a thickness d0 is formed. Next, in Step ST52, a heat treatment (annealing). is conducted for a certain period of time t with the predetermined temperature varied at T1, T2 and T3, and the resultant thicknesses d1, d2 and d3 of the amorphous region are measured. Then, in Step ST53, the recovery rates r (=d0−d1/t, d0−d2/t and d0−d3/t) of the amorphous region are calculated. Finally, in Step ST54, among a large number of data about the recovery rates as show n FIG. 18, a temperature corresponding to a recovery rate, which is most matched with the calculated recovery rate r, is selected, thereby determining the predetermined temperature T.

Specific Example 5

Next, a fifth specific example relating to the measurement of the distribution of temperatures within a wafer or a chamber using the spectroscopic ellipsometry will be described.

Figure 21:
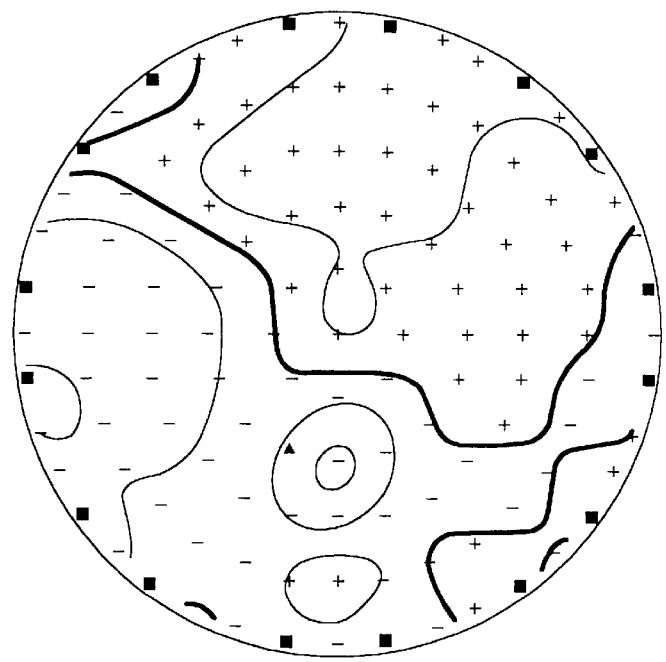
FIG. 21 is a diagram illustrating the distribution of thicknesses of an amorphous region in a wafer on the conditions for point A16 of FIG. 16 as data in a fifth specific example of the second embodiment.
Figure 22:
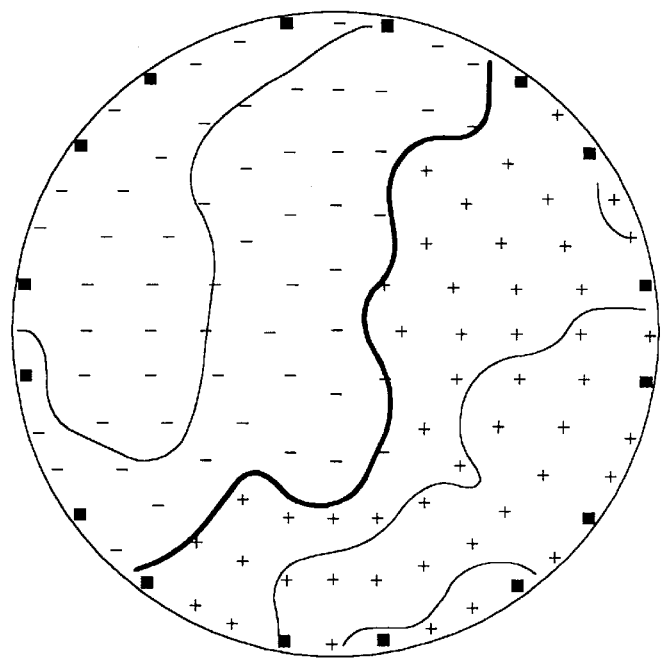
FIG. 22 is a diagram illustrating the distribution of thicknesses of an amorphous region in a wafer on the conditions for point C16 of FIG. 16 as data in the fifth specific example of the second embodiment.
Figure 23:
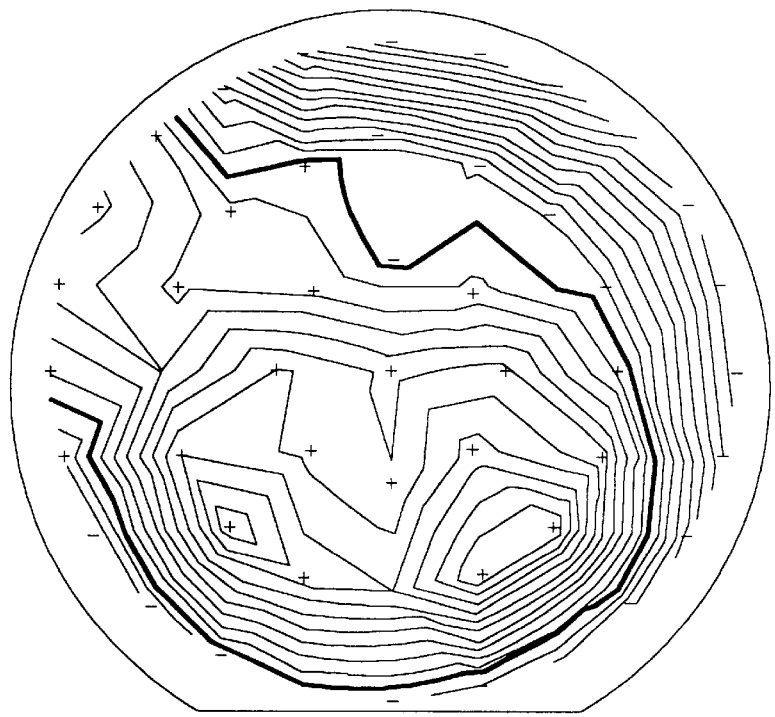
FIG. 23 is a diagram illustrating the distribution of temperatures in a wafer obtained by subtracting a thickness at each measurement point of FIG. 21 from a thickness at the corresponding measurement point of FIG. 22 as data in the fifth specific example of the second embodiment.

FIG. 21 is a thickness distribution diagram illustrating the in-plane uniformity of an amorphous region in a wafer placed in the state of the point A16 of FIG. 16. In this state, the average thickness is 44.785 nm, which is equal to the thickness at the point A16 of FIG. 16. The thickness at each point in the wafer is indicated to be larger (shown with +) or smaller (shown with −) than the average thickness. FIG. 22 is a thickness distribution diagram in an amorphous region in a wafer placed in the state of the point C16 of FIG. 16. In the same way as in FIG. 21, the thickness at each point in the wafer is indicated to be larger (shown with +) or smaller (shown with −) than the average thickness. In this state, the average thickness is 43.059 nm, which is equal to the thickness at the point C16 of FIG. 16. It can be seen that the thickness distribution shown in FIG. 22 is completely different from the thickness distribution of FIG. 21. FIG. 23 is a diagram illustrating the distribution of values, each obtained by subtracting the thickness at each measurement point shown in FIG. 21 from the thickness at the corresponding point shown in FIG. 22, and shows the variation in thickness at each point in 30 seconds. The decrease in thickness corresponds to a thickness changed from the amorphous state to the crystalline state, and it is shown how the decreases are distributed with respect to the average thickness (shown with a bold line) in the wafer plane.

The distribution of temperatures in a wafer plane can be derived by obtaining the distribution of decreases in thickness. Speaking more specifically, the annealing time is 30 seconds, and since the variation in average thickness can be obtained by subtracting the thickness at C16 (43.059 nm) from the thickness at A16 (44.785 nm), the decrease in thickness is (44.758−43.059)=1.726 nm. Accordingly, based on the data in FIG. 20, the annealing temperature can be obtained (275° C. in this case), and at the same time, the distribution of temperatures in the wafer plane can be derived from the distribution of the decreases in thickness in the wafer plane.

Specific Example 6

Next, a sixth specific example relating to the measurement of the distribution of film qualities in a wafer or a chamber using the spectroscopic ellipsometry will be described.

Figure 24:
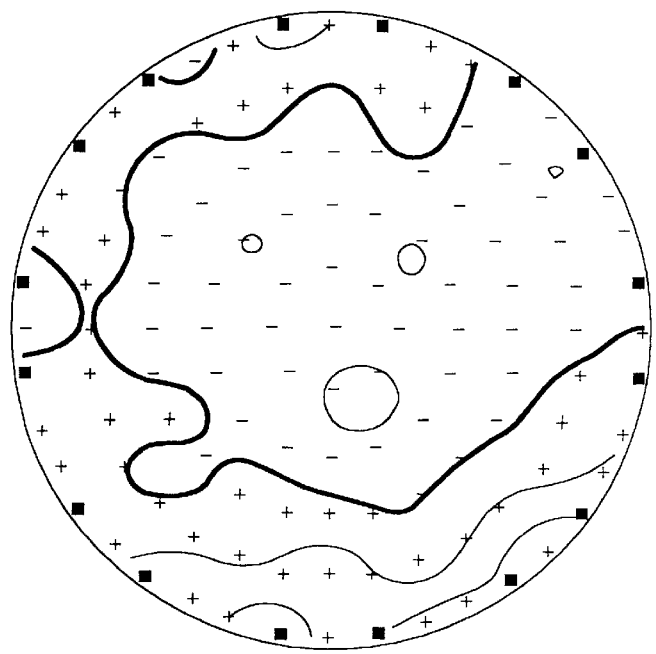
FIG. 24 is a diagram illustrating the distribution of absorption coefficients in an amorphous region in a wafer on the conditions for point A16 of FIG. 16 as data in a sixth specific example of the second embodiment.
Figure 25:
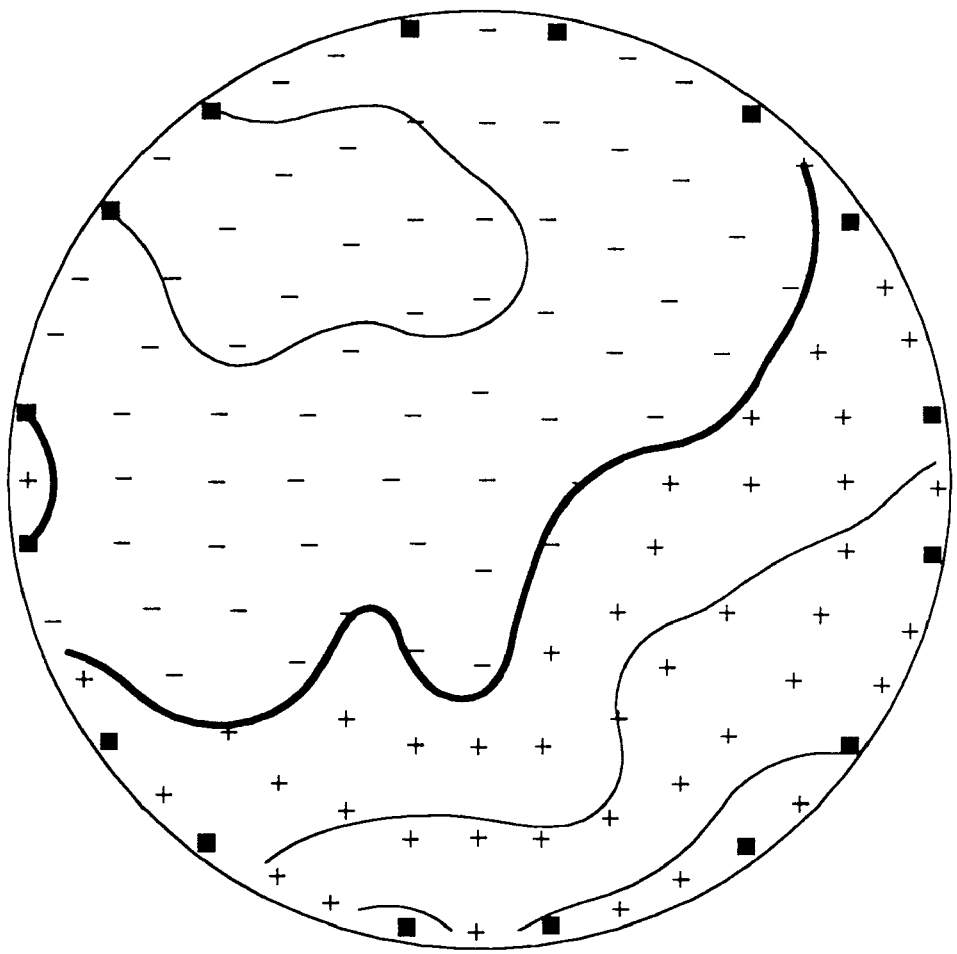
FIG. 25 is a diagram illustrating the distribution of absorption coefficients in an amorphous region in a wafer on the conditions for point C16 of FIG. 16 as data in the sixth specific example of the second embodiment.

FIG. 24 is a diagram illustrating the distribution of absorption coefficients in an amorphous region in a wafer placed in the state of the point A16 of FIG. 16. If an amorphous region has a large absorption coefficient, then the transparency thereof is necessarily high. That is to say, though the region is still amorphous, the region is closer to a crystalline state. Thus, the film quality of an amorphous region can be determined based on the absorption coefficient. There are various levels of amorphous states including one with a smaller degree of irregularity and closer to a crystalline state and one with a larger degree of irregularity and highly amorphous. Accordingly, the film quality is used as an index for distinguishing the difference. FIG. 25 is a diagram illustrating the distribution of absorption coefficients in an amorphous region in a wafer placed in the state of the point C16 of FIG. 16.

In this specific example, the distribution of the recovery states of the film quality in an amorphous region as a result of annealing can be derived from the distribution of absorption coefficients. Specifically, it is conventionally impossible to evaluate the in-plane uniformity in the recovery states of the film quality in an amorphous region as a result of low temperature annealing. However, according to the present invention, the in-plane uniformity of the film qualities in an amorphous region can be evaluated.

By utilizing the values or the in-wafer-plane distribution of absorption coefficients, the film quality of a region where silicide is formed (source/drain regions of an MOS transistor), for example, can be evaluated.

For example, since the film quality of an underlying semiconductor layer (source, drain or gate region) affects the reactivity in silicidation in a salicide process, it is significant to know the film quality of the semiconductor layer before the silicidation is performed. Accordingly, before a titanium film is deposited on an ion-implanted semiconductor layer (e.g., source/drain regions), the absorption coefficient of the semiconductor layer is measured, and the relationship between the absorption coefficient and the grain size of a silicide subsequently formed or the development of the silicidation is found beforehand. Then, the silicidation process can be appropriately controlled.

EMBODIMENT 3

In this embodiment, a method of controlling a fabrication process by utilizing the first embodiment or the first to sixth specific examples of the second embodiment will be described.

Specific Example 1

Figure 26A:
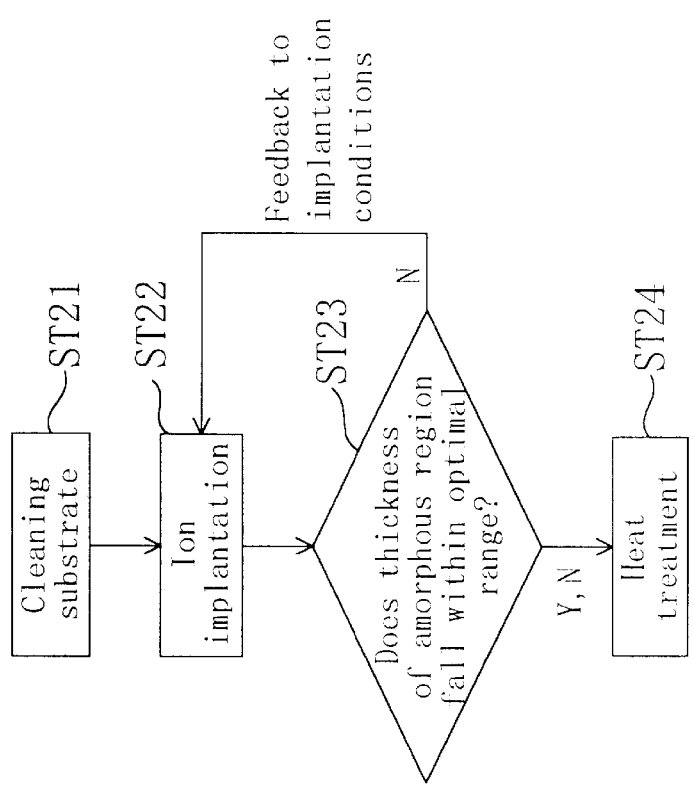
FIGS. 26(a) and 26(b) are flowcharts showing the procedures of determining whether or not an ion-implanted amorphous region is acceptable and modifying an ion implantation condition, respectively, in a first specific example of the third embodiment.
Figure 26B:
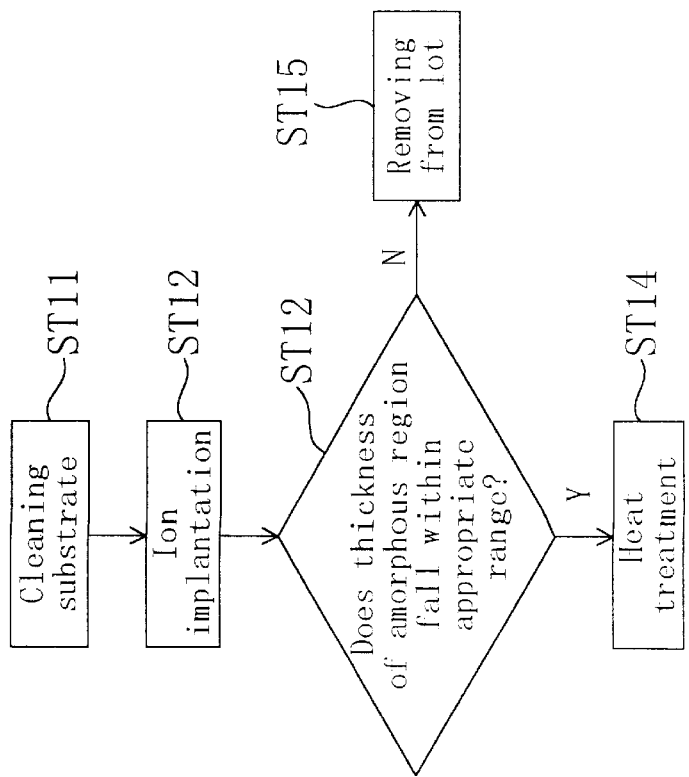

FIGS. 26(a) and 26(b) are flowcharts illustrating two methods of controlling an ion implantation step by utilizing the measurement of the thickness of an amorphous region according to the first embodiment.

In the method shown in FIG. 26(a), a substrate including a semiconductor layer is cleaned in Step ST11, and an amorphous region is formed in the semiconductor layer by implanting ions into the semiconductor layer in Step ST12. Next, in Step ST13, it is determined whether or not the thickness of the amorphous region falls within an appropriate range. If it is determined that the thickness of the amorphous region is within the appropriate range, the procedure proceeds to the next step ST14, where a heat treatment is conducted for activating the ions. Alternatively, if it is determined in Step ST13 that the thickness of the amorphous region is out of the appropriate range, the substrate is removed from the lot.

In accordance with this method, it is possible to avoid useless processing, which would other be performed on a defective substrate subsequently.

In accordance with the method shown in FIG. 26(b), a substrate including a semiconductor layer is cleaned in Step ST21, and an amorphous region is formed in the semiconductor layer by implanting ions into the semiconductor layer in Step ST22. Next, in Step ST23, it is determined whether or not the thickness of the amorphous region falls within an optimal range requiring no modification to the implantation conditions. If it is determined that the thickness of the amorphous region falls within the optimal range, the procedure proceeds to the next step ST24 without taking any action, where a heat treatment is conducted for activating the ions. Alternatively, if it is determined in Step ST23 that the thickness of the amorphous region is out of the optimal range, the implantation conditions for Step ST22 are modified so that the thickness of the amorphous region falls within the optimal range (by increasing the implant energy).

In accordance with this method, it is possible to retain the ion implantation conditions for the ion implantation step as optimal as possible. As a result, the yield can be improved, and subsequent procedures can be stabilized because the variation in thickness of the amorphous regions can be suppressed.

Alternately, it may be determined in Step ST23 whether or not the thickness of the amorphous region is equal to or larger than a lower limit. If the thickness of the amorphous region is equal to or larger than the lower limit, the procedure may proceed to the next step ST24. Conversely, if the thickness of the amorphous region is smaller than the lower limit, the procedure may return to step ST22, where ions are additionally implanted.

Specific Example 2

In this specific example, a method of controlling a film deposition step will be described. In this case, the following two methods are available.

In a first method, after a polysilicon film, a metal film, an insulating film or the like is deposited over an amorphous region in a substrate by CVD or sputtering, the film is removed by wet etching, for example. The spectroscopic ellipsometry is conducted before and after CVD or sputtering is performed, and the thicknesses of the amorphous region are compared before and after the process. In this manner, the temperature or the distribution of temperatures during CVD or sputtering can be derived. If the underlying amorphous region is affected during the removal of the film, an error, generated in the data because of the effect on the underlying amorphous region, may be corrected by repeating experiments. Specifically, the etched thickness of the amorphous region can be calculated based on an etching rate at which the amorphous region is removed. The etched thickness of the amorphous region may be confirmed by repeating the experiment several times and subtracted, whereby an accurate temperature for CVD or sputtering can be detected.

In a second method, if a film to be formed is transparent to measurement light (e.g., a silicon oxide or silicon nitride film), then the thickness of an amorphous region is measured with the transparent film formed on the amorphous region (i.e., in the shape of a two-layered film). In this manner, a temperature on the surface of a substrate during the film deposition is sensed.

Conventionally, there is no effective means for sensing a temperature on the surface of a substrate during CVD or sputtering. However, by utilizing the first to sixth specific examples of the second embodiment, a temperature on the surface of a substrate can be sensed for various types of CVD ranging from high temperature CVD to low temperature CVD. Accordingly, it is possible to properly set a temperature for appropriately retaining the temperature for CVD, specifically, plasma power and the like. Also, the distribution of temperatures within a chamber can also be sensed during CVD.

In any of the first and second methods, the data in FIG. 19 may be used if a high temperature heat treatment is involved.

Furthermore, in ashing a resist, the temperature rises to about 300° C. Accordingly, the temperature can be sensed based on the measured thickness of an amorphous region.

OTHER EMBODIMENTS

The measurement of the thickness and film quality of an amorphous region and an annealing temperature described in the foregoing embodiments can be automatically conducted by storing the procedures thereof in a storage medium.

For example, by storing the procedures of the first to fifth methods described in the first specific example of the first embodiment (such as the procedures shown in FIGS. 31 and 32) as a program in a computer readable storage medium, the thickness of an amorphous region formed by ion implantation can be automatically detected.

Alternatively, if the procedures for measuring a temperature by utilizing the thickness of an amorphous region described in the second embodiment (such as the procedures shown in FIGS. 27 through 29) are stored as a program in a computer readable storage medium, a temperature can be automatically detected during a process.

INDUSTRIAL APPLICABILITY

The present invention is applicable to the fabrication of semiconductor devices such as various types of transistors and semiconductor memories incorporated into electronic units.

What is claimed is:

1. An evaluation method of a semiconductor layer, comprising the steps of:

i) making linearly-polarized measurement light incident on the surface of the semiconductor layer at a tilt angle defined with respect to a normal crossing the surface at right angles, the semiconductor layer including an amorphous region with crystallinity disordered by dopant ions implanted into a substrate, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis;

ii) deriving at least $\cos\Delta$ as to the reflected ray of the measurement light reflected as an elliptically-polarized ray from the semiconductor layer, where $\Delta$ is a phase difference between p and s components;

iii) measuring a spectrum of at least the $\cos\Delta$ variable with a variation in the wavelength of the measurement light; and iv) estimating a physical quantity of the amorphous region based on at least the spectrum of the $\cos\Delta$.

2. The evaluation method of a semiconductor layer of claim 1, further comprising the step of calculating a reflection factor of the measurement light reflected from the amorphous region based on a ratio between the intensity of the incident ray and that of the reflected ray of the measurement light, wherein a film quality of the amorphous region is evaluated based on the reflection factor.

3. The evaluation method of a semiconductor layer of claim 1, wherein in the step iv), it is determined whether or not the amorphous region is present.

4. The evaluation method of a semiconductor layer of claim 1, wherein in the step iv), the thickness of the amorphous region is detected.

5. The evaluation method of a semiconductor layer of claim 4, further comprising the step of preparing a a correlation between at least the spectrum of $\cos\Delta$ and the thickness of the amorphous region, wherein in the step iv), the thickness of the amorphous region in the semiconductor layer is determined by reference to the correlation about at least the spectrum of $\cos\Delta$ obtained in the step ii).

6. The evaluation method of a semiconductor layer of claim 5, wherein, in the step of preparing the correlation, a relationship between implant energy and the thickness of the amorphous region and a relationship between the spectrum of $\cos\Delta$ and implant energy are prepared as first and second correlations, respectively, with regard to each particular ion implant dose, and wherein in the step iv), after the implant energy of the ions implanted into the semiconductor layer has been obtained by reference to the second correlation about the spectrum of $\cos\Delta$ obtained in the step ii), the thickness of the amorphous region in the semiconductor layer is determined by reference to the first correlation about the implant energy obtained.

7. The evaluation method of a semiconductor layer of claim 5, wherein, in the step of preparing the correlation, a relationship between an ion implant dose and the thickness of the amorphous region and a relationship between the spectrum of $\cos\Delta$ and an ion implant dose are prepared as first and second correlations, respectively, with regard to each particular implant energy, and wherein in the step iv), after the implant dose of the ions implanted into the semiconductor layer has been obtained by reference to the second correlation about the spectrum of $\cos\Delta$ obtained in the step ii), the thickness of the amorphous region in the semiconductor layer is determined by reference to the first correlation about the ion implant dose obtained.

8. The evaluation method of a semiconductor layer of claim 5, wherein, in the step of preparing the correlation, a relationship between implant energy and the thickness of the amorphous region is prepared as a first correlation with regard to each particular ion implant dose, and a relationship between a wavelength corresponding to a local maximum of $\cos\Delta$ within a predetermined wavelength region of the spectrum of $\cos\Delta$ and implant energy is prepared as a second correlation, the wavelength region being defined by making the ion implant dose constant and the implant energy variable, and wherein in the step iv), after the implant energy of the ions implanted into the semiconductor layer has been obtained by reference to the second correlation about the spectrum of $\cos\Delta$ obtained in the step ii), the thickness of the amorphous region in the semiconductor layer is determined by reference to the first correlation about the implant energy obtained.

9. The evaluation method of a semiconductor layer of claim 5, wherein, in the step of preparing the correlation, a relationship between an implant dose and the thickness of the amorphous region is prepared as a first correlation with regard to each particular implant energy, and a relationship between a wavelength corresponding to a local maximum of $\cos\Delta$ within a predetermined wavelength region of the spectrum of $\cos\Delta$ and an implant dose is prepared as a second correlation, the wavelength region being defined by making the implant energy constant and the implant dose variable, and wherein in the step iv), after the implant dose of the ions implanted into the semiconductor layer has been obtained by reference to the second correlation about the spectrum of $\cos\Delta$ obtained in the step ii), the thickness of the amorphous region in the semiconductor layer is determined by reference to the first correlation about the ion implant dose obtained.

10. The evaluation method of a semiconductor layer of claim 4, wherein the distribution of thicknesses of a plurality of amorphous regions in the semiconductor layer is measured by performing the steps i) through iv) on the amorphous regions in the semiconductor layer.

11. The evaluation method of a semiconductor layer of claim 1, wherein, in the step iv), the degree of recovery of the amorphous region responsive to ion beams is estimated.

12. The evaluation method of a semiconductor layer of claim 1, wherein, in the step iv), the performance of implanters are evaluated based on at least the spectra of $\cos\Delta$ of two amorphous regions formed using two different implanters on the same implant conditions.

13. The evaluation method of a semiconductor layer of claim 1, further comprising the steps of:

deriving $\tan\psi$ as to the reflected ray of the measurement light, where $\psi$ is a ratio of the amplitude of a p component to that of an s component; and measuring the spectrum of the $\tan\psi$ with the wavelength of the measurement light varied, wherein, in the step of estimating the physical quantity of the amorphous region, the physical quantity of the amorphous region is estimated with the shape of the spectrum of the $\tan\psi$ taken into consideration.

14. The evaluation method of a semiconductor layer of claim 4, wherein, a first thickness of the amorphous region is determined by performing the steps i) through iv) on the semiconductor layer before a heat holding process is conducted, the method further comprising the steps of:

determining a second thickness of the amorphous region by performing the steps i) through iv) on the semiconductor layer after the heat holding process has been conducted on the semiconductor layer; and measuring a temperature of the heat holding process based on a recovery rate derived from the first and second thicknesses of the amorphous region and a time of the heat holding process.

15. The evaluation method of a semiconductor layer of claim 14, further comprising the step of finding a correlation between a temperature of the heat holding process conducted at a temperature equal to or lower than 450° C. and a decrease in thickness of an amorphous region, wherein, in the step iv), the temperature of the heat holding process is measured based on the correlation.

16. The evaluation method of a semiconductor layer of claim 14, wherein the temperature of the heat holding process is measured as to each of a plurality of amorphous regions in the substrate, and wherein the distribution of temperatures in the substrate or in a processing system is measured based on the temperatures held at the amorphous regions.

17. A method for fabricating a semiconductor device on a semiconductor layer in a substrate, the method comprising the steps of:

i) forming an amorphous region with crystallinity disordered by implanting dopant ions into the semiconductor layer;

ii) making linearly-polarized measurement light incident on the surface of the semiconductor layer, where the amorphous region has been formed, at a tilt angle defined with respect to a normal crossing the surface at right angles, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis, and measuring at least the spectrum of $\cos\Delta$ in accordance with a variation in the wavelength of the measurement light as to the reflected ray of the measurement light reflected as an elliptically-polarized ray from the semiconductor layer, where $\Delta$ is a phase difference between p and s components; and iii) estimating a physical quantity of the amorphous region based on at least the spectrum of the $\cos\Delta$ obtained in the step ii).

18. The method for fabricating a semiconductor device of claim 17, further comprising the step of preparing a correlation between the thickness of the amorphous region and at least the spectrum of $\cos\Delta$, wherein, in the step iii), the thickness of the amorphous region in the semiconductor layer is determined by reference to the correlation about at least the spectrum of $\cos\Delta$ obtained in the step ii).

19. The method for fabricating a semiconductor device of claim 18, further comprising the step of changing ion implantation conditions for the step ii) based on the result of evaluation of the physical quantity of the amorphous region obtained in the step iii).

20. The method for fabricating a semiconductor device of claim 18, further comprising the step of determining whether or not the substrate including the amorphous region is acceptable based on the result of evaluation of the physical quantity of the amorphous region obtained in the step iii).

21. A method for fabricating a semiconductor device on a semiconductor layer in a substrate, the method comprising the steps of:

i) forming an amorphous region with crystallinity disordered by implanting dopant ions into the semiconductor layer;

ii) conducting a process of holding the temperature of the amorphous region at a predetermined temperature;

iii) making linearly-polarized measurement light incident on the surface of the semiconductor layer at a tilt angle defined with respect to a normal crossing the surface at right angles, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis, and measuring at least the spectrum of $\cos\Delta$ in accordance with a variation in the wavelength of the measurement light as to the reflected ray of the measurement light reflected as an elliptically-polarized ray from the semiconductor layer, where $\Delta$ is a phase difference between p and s components; and iv) estimating a physical quantity of the amorphous region based on at least the spectrum of $\cos\Delta$ obtained in the step iii).

22. The method for fabricating a semiconductor device of claim 21, further comprising the step of preparing a correlation between the thickness of the amorphous region and at least the spectrum of $\cos\Delta$, wherein, in the step iv), the thickness of the amorphous region in the semiconductor layer is determined by reference to the correlation about at least the spectrum of $\cos\Delta$ obtained in the step ii).

23. The method for fabricating a semiconductor device of claim 22, further comprising the steps of:

estimating the thickness of the amorphous region prior to the step ii) by performing the same process steps as the steps iii) and iv) posterior to the step i) and prior to the step ii); and obtaining a variation in the thickness of the amorphous region before and after the step ii) is performed.

24. The method for fabricating a semiconductor device of claim 21, wherein in the step iv), a reflection factor of the measurement light reflected from the amorphous region is calculated based on a ratio between the intensity of the incident and reflected rays of the measurement light, and film quality of the amorphous region is evaluated based on the reflection factor.

25. A method for fabricating a semiconductor device on a semiconductor layer in a substrate, the method comprising the steps of:

i) forming an amorphous region with crystallinity disordered by implanting dopant ions into the semiconductor layer;

ii) conducting a process of holding the temperature of the amorphous region at a predetermined temperature;

iii) making linearly-polarized measurement light incident on the surface of the semiconductor layer at a tilt angle defined with respect to a normal crossing the surface at right angles, the measurement light being tilted relative to p and s directions in a plane vertical to the optical axis thereof, the p direction being defined by an intersection between the plane vertical to the optical axis and a plane containing incident and reflected rays, the s direction being vertical to the p direction in the plane vertical to the optical axis, and measuring at least the spectra of $\cos\Delta$ before and after the process in the step ii) is performed as to the reflected ray of the measurement light reflected as an elliptically-polarized ray from the semiconductor layer, where Δ is a phase difference between p and s components;

iv) measuring a variation in the thickness of the amorphous region before and after the process in the step ii) is performed based on at least the variation in the spectrum of cosΔ; and v) measuring a temperature of the heat holding process based on a recovery rate calculated based on the variation in the thickness of the amorphous region before and after the process is performed and a time of the heat holding process.

26. The method for fabricating a semiconductor device of claim 25, further comprising the step of preparing a correlation between a temperature of the heat holding process conducted at a temperature equal to or lower than 450° C. and a decrease in thickness of the amorphous region, wherein, in the step iv), the temperature of the heat holding process is measured based on the correlation.

27. A computer readable storage medium used for estimating a physical quantity of an amorphous region based on at least the spectrum of cosΔ in accordance with a variation in the wavelength of measurement light, the amorphous region being located in a semiconductor layer in a substrate, the crystallinity of the amorphous region having been disordered by the implantation of dopant ions into the substrate, the measurement light having been incident on the semiconductor layer at an angle tilted relative to p and s directions in a plane vertical to the optical axis thereof and having been reflected as an elliptically-polarized ray from the semiconductor layer, the p direction being defined by an intersection between the plane vertical to the optical axis and a plane containing incident and reflected rays, the s direction being vertical to the p direction in the plane vertical to the optical axis, Δ being a phase difference between p and s components as to the reflected ray, the storage medium storing a program for making a computer execute the procedures of:

i) storing a correlation between the thickness of the amorphous region and at least the spectrum of cosΔ;

ii) inputting at least the spectrum of the cosΔ as a measurement result obtained by a spectroscopic ellipsometry performed on the amorphous region formed on specific implant conditions; and iii) fetching the correlation and determining the thickness of the amorphous region in the semiconductor layer by reference to the correlation about at least the spectrum of cosΔ obtained in the step ii).

28. The storage medium of claim 27, wherein, in the procedure i), a relationship between implant energy and the thickness of the amorphous region and a relationship between the spectrum of cosΔ and implant energy are stored as first and second correlations, respectively, with regard to each particular ion implant dose, and wherein in the procedure iii), after the implant energy of the ions implanted into the semiconductor layer has been obtained by reference to the second correlation about the spectrum of cosΔ input in the procedure ii), the thickness of the amorphous region in the semiconductor layer is determined by reference to the first correlation about the implant energy obtained.

29. The storage medium of claim 27, wherein, in the procedure i), a relationship between an ion implant dose and the thickness of the amorphous region and a relationship between the spectrum of cosΔ and an ion implant dose are stored as first and second correlations, respectively, with regard to each particular implant energy, and wherein in the procedure iii), after the implant dose of the ions implanted into the semiconductor layer has been obtained by reference to the second correlation about the spectrum of cosΔ input in the procedure ii), the thickness of the amorphous region in the semiconductor layer is determined by reference to the first correlation about the ion implant dose obtained.

30. A computer readable storage medium used for measuring a temperature of a heat treatment conducted on a semiconductor layer in a substrate based on at least the spectrum of cosΔ in accordance with a variation in the wavelength of measurement light, the semiconductor layer including an amorphous region with crystallinity disordered by the implantation of dopant ions into the substrate, the measurement light having been incident on the semiconductor layer at an angle tilted relative to p and s directions in a plane vertical to the optical axis thereof and having been reflected as an elliptically-polarized ray from the semiconductor layer, the p direction being defined by an intersection between the plane vertical to the optical axis and a plane containing incident and reflected rays, the s direction being vertical to the p direction in the plane vertical to the optical axis, Δ being a phase difference between p and s components as to the reflected ray, the storage medium storing a program for making a computer execute the procedures of:

i) storing a relationship between a time of the heat treatment and a decrease in thickness of the amorphous region at a particular temperature as a correlation;

ii) storing a thickness of the amorphous region prior to the heat treatment;

iii) storing a thickness of the amorphous region posterior to the heat treatment; and iv) fetching the thicknesses of the amorphous region measured before and after the heat treatment is conducted and the correlation, and obtaining the temperature of the heat treatment by reference to the correlation about the decrease in thickness of the amorphous region before and after the heat treatment is conducted.

31. A computer readable storage medium used for measuring a temperature of a heat treatment conducted on a semiconductor layer in a substrate based on at least the spectrum of cosΔ in accordance with a variation in the wavelength of measurement light, the semiconductor layer including an amorphous region with crystallinity disordered by the implantation of dopant ions into the substrate, the measurement light having been incident on the semiconductor layer at an angle tilted relative to p and s directions in a plane vertical to the optical axis thereof and having been reflected as an elliptically-polarized ray from the semiconductor layer, the p direction being defined by an intersection between the plane vertical to the optical axis and a plane containing incident and reflected rays, the s direction being vertical to the p direction in the plane vertical to the optical axis, Δ being a phase difference between p and s components as to the reflected ray, the storage medium storing a program for making a computer execute the procedures of:

i) storing a recovery rate as a correlation for each particular temperature, the recovery rate being obtained based on a relationship between a time of the heat treatment and a decrease in thickness of the amorphous region at each said particular temperature;

ii) storing a thickness of the amorphous region prior to the heat treatment;

iii) storing a thickness of the amorphous region posterior to the heat treatment and a time of the heat treatment; and iv) fetching a decrease in thickness of the amorphous region before and after the heat treatment and the correlation, and obtaining the temperature of the heat treatment by reference to the correlation about the recovery rate obtained by dividing the decrease in thickness of the amorphous region before and after the heat treatment by the time of the heat treatment.

32. A computer readable storage medium used for measuring a temperature of a heat treatment conducted on a semiconductor layer in a substrate based on at least the spectrum of cos$\Delta$ in accordance with a variation in the wavelength of measurement light, the semiconductor layer including an amorphous region with crystallinity disordered by the implantation of dopant ions into the substrate, the measurement light having been incident on the semiconductor layer at an angle tilted relative to p and s directions in a plane vertical to the optical axis thereof and having been reflected as an elliptically-polarized ray from the semiconductor layer, the p direction being defined by an intersection between the plane vertical to the optical axis and a plane containing incident and reflected rays, the s direction being vertical to the p direction in the plane vertical to the optical axis, $\Delta$ being a phase difference between p and s components as to the reflected ray, the storage medium storing a program for making a computer execute the procedures of:

i) storing a recovery rate as a correlation, the recovery rate being obtained based on a relationship between a temperature of the heat treatment and a variation in thickness of the amorphous region at a particular time;

ii) storing a thickness of the amorphous region prior to the heat treatment;

iii) storing a thickness of the amorphous region posterior to the heat treatment and a time of the heat treatment; and iv) fetching a decrease in thickness of the amorphous region before and after the heat treatment and the correlation, and obtaining the temperature of the heat treatment by reference to the correlation about the recovery rate obtained by dividing the decrease in thickness of the amorphous region before and after the heat treatment by the time of the heat treatment.

33. The evaluation method of a semiconductor layer of claim 15, wherein the temperature of the heat holding process is measured as to each of a plurality of amorphous regions in the substrate, and wherein the distribution of temperatures in the substrate or in a processing system is measured based on the temperatures held at the amorphous regions.

\* \* \* \* \*